United States Patent
Singh et al.

(10) Patent No.: US 10,238,848 B2
(45) Date of Patent: Mar. 26, 2019

(54) SOLVENT-CAST MICROPROTRUSION ARRAYS CONTAINING ACTIVE INGREDIENT

(71) Applicant: Corium International, Inc., Menlo Park, CA (US)

(72) Inventors: Parminder Singh, Union City, CA (US); Robert Wade Worsham, Sutter Creek, CA (US); Joseph C. Trautman, Sunnyvale, CA (US); Danir Bayamov, Irvine, CA (US); Danny Lee Bowers, Lake Odessa, MI (US); Andrew Richard Klemm, Ada, MI (US); Steven Richard Klemm, Grand Rapids, MI (US); Guohua Chen, Sunnyvale, CA (US)

(73) Assignee: Corium International, Inc., Menlo Park, CA (US)

( * ) Notice: Subject to any disclaimer, the term of this patent is extended or adjusted under 35 U.S.C. 154(b) by 612 days.

(21) Appl. No.: 14/789,919

(22) Filed: Jul. 1, 2015

(65) Prior Publication Data

US 2015/0297878 A1    Oct. 22, 2015

Related U.S. Application Data

(63) Continuation of application No. 12/148,180, filed on Apr. 16, 2008, now Pat. No. 9,114,238.
(Continued)

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0021* (2013.01); *A61K 38/29* (2013.01);
(Continued)

(58) Field of Classification Search
CPC .... A61K 38/29; A61K 38/385; A61K 9/0021; A61M 2037/0046; A61M 2037/0053;
(Continued)

(56) References Cited

U.S. PATENT DOCUMENTS

| | | |
|---|---|---|
| 1,554,510 A | 9/1925 | Kirby |
| 1,770,632 A | 7/1930 | Smith |

(Continued)

FOREIGN PATENT DOCUMENTS

| | | |
|---|---|---|
| CA | 2205444 | 6/1996 |
| CA | 2376285 | 12/2000 |

(Continued)

OTHER PUBLICATIONS

"Eudragit EPO Readymix—Taste masking and moisture protection have never been easier" Evonik Industries, Evonik Industries AG, Pharma Polymers & Services, Nov. 2014.
(Continued)

*Primary Examiner* — Imani Hayman
(74) *Attorney, Agent, or Firm* — McDermott Will & Emery LLP

(57) ABSTRACT

In an aspect of the invention, an array of microprotrusions is formed by providing a mold with cavities corresponding to the negative of the microprotrusions, casting atop the mold a first solution comprising a biocompatible material and a solvent, removing the solvent, casting a second solution atop the first cast solution, removing the solvent from the second solution, and demolding the resulting array from the mold. The first solution preferably contains an active ingredient.

18 Claims, 5 Drawing Sheets

Related U.S. Application Data

(60) Provisional application No. 60/925,262, filed on Apr. 18, 2007, provisional application No. 60/923,861, filed on Apr. 16, 2007.

(51) Int. Cl.
  *A61K 38/29* (2006.01)
  *A61K 38/38* (2006.01)

(52) U.S. Cl.
  CPC ... *A61K 38/385* (2013.01); *A61M 2037/0046* (2013.01); *A61M 2037/0053* (2013.01); *A61M 2037/0061* (2013.01); *A61M 2202/0007* (2013.01); *A61M 2202/07* (2013.01); *A61M 2202/30* (2013.01); *A61M 2207/00* (2013.01)

(58) Field of Classification Search
  CPC .. A61M 2037/0061; A61M 2202/0007; A61M 2202/07; A61M 2202/30; A61M 2207/00; A61M 37/0015
  See application file for complete search history.

(56) References Cited

U.S. PATENT DOCUMENTS

| | | |
|---|---|---|
| 2,046,240 A | 6/1936 | Bayley |
| 2,434,407 A | 1/1948 | George |
| 3,675,766 A | 7/1972 | Rosenthal |
| 3,704,194 A | 11/1972 | Harrier et al. |
| 3,814,097 A | 6/1974 | Ganderton et al. |
| 3,873,255 A | 3/1975 | Kalwaites |
| 3,918,449 A | 11/1975 | Pistor |
| 3,964,482 A | 6/1976 | Gerstel et al. |
| 4,055,029 A | 10/1977 | Kalbow |
| 4,117,841 A | 10/1978 | Perrotta et al. |
| 4,151,240 A | 4/1979 | Lucas et al. |
| 4,180,232 A | 12/1979 | Hardigg |
| 4,342,314 A | 8/1982 | Radel et al. |
| 4,381,963 A | 5/1983 | Goldstein et al. |
| 4,395,215 A | 7/1983 | Bishop |
| 4,402,696 A | 9/1983 | Gulko |
| 4,460,368 A | 7/1984 | Allison et al. |
| 4,460,370 A | 7/1984 | Allison et al. |
| 4,463,045 A | 7/1984 | Ahr et al. |
| 4,509,908 A | 4/1985 | Mullane, Jr. |
| 4,515,168 A | 5/1985 | Chester et al. |
| 4,556,441 A | 12/1985 | Faasse, Jr. |
| 4,585,991 A | 4/1986 | Reid et al. |
| 4,597,961 A | 7/1986 | Etscorn |
| 4,609,518 A | 9/1986 | Curro et al. |
| 4,630,603 A | 12/1986 | Greenway |
| 4,660,721 A | 4/1987 | Mykleby |
| 4,695,422 A | 9/1987 | Curro et al. |
| 4,743,234 A | 5/1988 | Leopoldi et al. |
| 4,743,249 A | 5/1988 | Loveland |
| 4,784,737 A | 11/1988 | Ray et al. |
| 4,812,305 A | 3/1989 | Vocal |
| 4,837,049 A | 6/1989 | Byers et al. |
| 4,846,821 A | 7/1989 | Lyons et al. |
| 4,904,475 A | 2/1990 | Gale et al. |
| 4,996,159 A | 2/1991 | Glaser |
| 5,051,259 A | 9/1991 | Olsen et al. |
| 5,061,258 A | 10/1991 | Martz |
| 5,134,079 A | 7/1992 | Cusak et al. |
| 5,139,029 A | 8/1992 | Fishman et al. |
| 5,156,591 A | 10/1992 | Gross et al. |
| 5,158,073 A | 10/1992 | Bukowski |
| 5,160,315 A | 11/1992 | Heinecke et al. |
| 5,162,043 A | 11/1992 | Lew et al. |
| 5,163,918 A | 11/1992 | Righi et al. |
| 5,190,558 A | 3/1993 | Matsushita et al. |
| 5,198,192 A | 3/1993 | Saito et al. |
| 5,215,088 A | 6/1993 | Normann et al. |
| 5,244,677 A | 9/1993 | Kreckel et al. |
| 5,244,711 A | 9/1993 | Drelich et al. |
| 5,250,023 A | 10/1993 | Lee et al. |
| 5,250,067 A | 10/1993 | Gelfer et al. |
| 5,252,279 A | 10/1993 | Gore et al. |
| 5,256,360 A | 10/1993 | Li |
| 5,279,544 A | 1/1994 | Gross et al. |
| 5,308,625 A | 5/1994 | Wong et al. |
| 5,318,557 A | 6/1994 | Gross |
| 5,320,600 A | 6/1994 | Lambert |
| 5,330,452 A | 7/1994 | Zook |
| 5,362,307 A | 11/1994 | Guy et al. |
| 5,383,512 A | 1/1995 | Jarvis |
| 5,457,041 A | 10/1995 | Ginaven et al. |
| 5,462,743 A | 10/1995 | Turner et al. |
| 5,476,443 A | 12/1995 | Cartmell et al. |
| 5,487,726 A | 1/1996 | Rabineau et al. |
| 5,496,304 A | 3/1996 | Chasan |
| 5,498,235 A | 3/1996 | Flower |
| 5,503,843 A | 4/1996 | Santus et al. |
| 5,512,219 A | 4/1996 | Rowland et al. |
| 5,520,629 A | 5/1996 | Heinecke et al. |
| 5,527,287 A | 6/1996 | Miskinyar |
| 5,527,288 A | 6/1996 | Gross et al. |
| 5,531,675 A | 7/1996 | Yoo |
| 5,531,855 A | 7/1996 | Heinecke et al. |
| 5,536,263 A | 7/1996 | Rolf et al. |
| 5,551,953 A | 9/1996 | Lattin et al. |
| 5,567,376 A | 10/1996 | Turi et al. |
| 5,569,469 A | 10/1996 | Lovrechich |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,662,127 A | 9/1997 | De Vaughn |
| 5,676,850 A | 10/1997 | Reed et al. |
| 5,681,580 A | 10/1997 | Jang et al. |
| 5,697,901 A | 12/1997 | Eriksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,730,721 A | 3/1998 | Hyatt et al. |
| 5,735,273 A | 4/1998 | Kurnik et al. |
| 5,738,642 A | 4/1998 | Heinecke et al. |
| 5,756,117 A | 5/1998 | D'Angelo et al. |
| 5,771,890 A | 6/1998 | Tamada |
| 5,788,983 A | 8/1998 | Chien et al. |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,843,114 A | 12/1998 | Jang |
| 5,848,985 A | 12/1998 | Muroki |
| 5,848,990 A | 12/1998 | Cirelli et al. |
| 5,848,991 A | 12/1998 | Gross et al. |
| 5,851,549 A | 12/1998 | Svec |
| 5,855,801 A | 1/1999 | Lin et al. |
| 5,868,244 A | 2/1999 | Ivanov et al. |
| 5,873,849 A | 2/1999 | Bernard |
| 5,879,326 A | 3/1999 | Godshall et al. |
| 5,900,252 A | 5/1999 | Calanchi et al. |
| 5,932,240 A | 8/1999 | D'Angelo et al. |
| 5,938,684 A | 8/1999 | Lynch et al. |
| 5,948,488 A | 9/1999 | Marecki et al. |
| 5,962,011 A | 10/1999 | Devillez et al. |
| 5,964,729 A | 10/1999 | Choi et al. |
| 5,983,136 A | 11/1999 | Kamen |
| 5,987,989 A | 11/1999 | Yamamoto et al. |
| 5,997,549 A | 12/1999 | Sauceda et al. |
| 5,997,986 A | 12/1999 | Turi et al. |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,038,485 A | 3/2000 | Axelgaard |
| 6,047,208 A | 4/2000 | Flower |
| 6,050,988 A | 4/2000 | Zuck |

(56) References Cited

U.S. PATENT DOCUMENTS

| | | |
|---|---|---|
| 6,055,453 A | 4/2000 | Hofmann et al. |
| 6,080,172 A | 6/2000 | Fujiwara et al. |
| 6,083,196 A | 7/2000 | Trautman et al. |
| 6,091,975 A | 7/2000 | Daddona et al. |
| 6,106,751 A | 8/2000 | Talbot et al. |
| 6,120,792 A | 9/2000 | Juni |
| 6,129,696 A | 10/2000 | Sibalis |
| 6,132,449 A | 10/2000 | Lum et al. |
| 6,132,755 A | 10/2000 | Eicher et al. |
| 6,135,990 A | 10/2000 | Heller et al. |
| 6,136,008 A | 10/2000 | Becker et al. |
| 6,156,336 A | 12/2000 | Bracht |
| 6,169,224 B1 | 1/2001 | Heinecke et al. |
| 6,181,964 B1 | 1/2001 | Hofmann et al. |
| 6,183,434 B1 | 2/2001 | Eppstein |
| 6,183,770 B1 | 2/2001 | Muchin et al. |
| 6,187,210 B1 | 2/2001 | Lebouitz et al. |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,248,120 B1 | 6/2001 | Wyszogrodzki |
| 6,256,533 B1 | 7/2001 | Yuzhakov et al. |
| 6,293,925 B1 | 9/2001 | Safabash et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,355,054 B1 | 3/2002 | Neuberger |
| 6,375,627 B1 | 4/2002 | Mauze et al. |
| 6,375,870 B1 | 4/2002 | Visovsky et al. |
| 6,375,978 B1 | 4/2002 | Kliener et al. |
| 6,379,324 B1 | 4/2002 | Garstein et al. |
| 6,440,096 B1 | 8/2002 | Lastovich et al. |
| 6,451,240 B1 | 9/2002 | Sherman et al. |
| 6,471,903 B2 | 10/2002 | Sherman et al. |
| 6,476,288 B1 | 11/2002 | Van Rijswijck et al. |
| 6,485,470 B2 | 11/2002 | Hostettler et al. |
| 6,494,830 B1 | 12/2002 | Wessel |
| 6,503,231 B1 | 1/2003 | Prausnitz et al. |
| 6,508,947 B2 | 1/2003 | Gulvin et al. |
| 6,511,463 B1 | 1/2003 | Wood et al. |
| 6,512,626 B1 | 1/2003 | Schmidt |
| 6,516,223 B2 | 2/2003 | Hofmann |
| 6,532,386 B2 | 3/2003 | Sun et al. |
| 6,533,884 B1 | 3/2003 | Mallik |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whiston |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 | 6/2004 | Prausnitz et al. |
| 6,767,341 B2 | 7/2004 | Cho |
| 6,770,480 B1 | 8/2004 | Canham |
| 6,778,853 B1 | 8/2004 | Heller et al. |
| 6,780,171 B2 | 8/2004 | Gabel et al. |
| 6,808,506 B2 | 10/2004 | Lastovich et al. |
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho et al. |
| 6,991,809 B2 | 1/2006 | Anderson |
| 7,011,844 B2 | 3/2006 | Gale et al. |
| 7,048,723 B1 | 5/2006 | Frazier et al. |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,128,730 B2 | 10/2006 | Marano-Ford et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,419,481 B2 | 9/2008 | Trautman et al. |
| 7,572,405 B2 | 8/2009 | Sherman et al. |
| 7,578,954 B2 | 8/2009 | Gartstein et al. |
| 7,578,985 B2 | 8/2009 | Aderhold et al. |
| 7,611,481 B2 | 11/2009 | Cleary et al. |
| 7,658,728 B2 | 2/2010 | Yuzhakov |
| 7,678,777 B2 | 3/2010 | Yasuda et al. |
| 7,763,203 B2 | 7/2010 | Arias et al. |
| 7,785,301 B2 | 8/2010 | Yuzhakov |
| 7,789,733 B2 | 9/2010 | Sugimura |
| 7,798,987 B2 | 9/2010 | Trautman et al. |
| 7,828,827 B2 | 11/2010 | Gartstein et al. |
| 7,846,488 B2 | 12/2010 | Johnson |
| 7,914,480 B2 | 3/2011 | Cleary et al. |
| 8,057,842 B2 | 11/2011 | Choi et al. |
| 8,062,573 B2 | 11/2011 | Kwon |
| 8,216,190 B2 | 7/2012 | Gartstein et al. |
| 8,267,889 B2 | 9/2012 | Cantor et al. |
| 8,366,677 B2 | 2/2013 | Kaspar et al. |
| 8,696,638 B2 | 4/2014 | Terahara et al. |
| 8,702,726 B2 | 4/2014 | Gartstein et al. |
| 8,734,697 B2 | 5/2014 | Chen et al. |
| 8,747,362 B2 | 6/2014 | Terahara |
| 8,771,781 B2 | 7/2014 | Tokumoto et al. |
| 8,821,446 B2 | 9/2014 | Trautman et al. |
| 8,834,423 B2 | 9/2014 | Falo, Jr. et al. |
| 8,900,180 B2 | 12/2014 | Wolter et al. |
| 8,911,749 B2 | 12/2014 | Gharty-Tagoe et al. |
| 9,114,238 B2 | 8/2015 | Singh et al. |
| 9,220,678 B2 | 12/2015 | Kendall et al. |
| 9,452,280 B2 | 9/2016 | Singh et al. |
| 9,498,524 B2 | 11/2016 | Ghartey-Tagoe et al. |
| 9,549,746 B2 | 1/2017 | Woolfsen et al. |
| 9,687,640 B2 | 6/2017 | Trautman et al. |
| 9,687,641 B2 | 6/2017 | Singh et al. |
| 2001/0023324 A1 | 9/2001 | Pronovost et al. |
| 2001/0023351 A1 | 9/2001 | Eilers et al. |
| 2002/0006355 A1 | 1/2002 | Whitson |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0123675 A1 | 9/2002 | Trautman et al. |
| 2002/0128599 A1 | 9/2002 | Cormier et al. |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |

(56) References Cited

U.S. PATENT DOCUMENTS

| | | |
|---|---|---|
| 2002/0188245 A1 | 12/2002 | Martin et al. |
| 2002/0188310 A1 | 12/2002 | Seward et al. |
| 2002/0193729 A1 | 12/2002 | Cormier et al. |
| 2002/0193819 A1 | 12/2002 | Porter et al. |
| 2003/0083645 A1 | 5/2003 | Angel et al. |
| 2003/0093028 A1 | 5/2003 | Spiegel |
| 2003/0093089 A1 | 5/2003 | Greenberg |
| 2003/0135167 A1 | 7/2003 | Gonnelli |
| 2003/0166624 A1 | 9/2003 | Gale et al. |
| 2003/0187394 A1 | 10/2003 | Wilkinson et al. |
| 2003/0195474 A1 | 10/2003 | Down et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 | 11/2003 | Lastovich et al. |
| 2003/0220656 A1 | 11/2003 | Gartstein et al. |
| 2004/0049150 A1 | 3/2004 | Dalton et al. |
| 2004/0053894 A1 | 3/2004 | Mazess et al. |
| 2004/0062813 A1 | 4/2004 | Cormier et al. |
| 2004/0087893 A1 | 5/2004 | Kwon |
| 2004/0087992 A1 | 5/2004 | Gartstein et al. |
| 2004/0096455 A1 | 5/2004 | Maa et al. |
| 2004/0106904 A1 | 6/2004 | Gonnelli et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho |
| 2004/0204669 A1 | 10/2004 | Hofmann |
| 2004/0220535 A1 | 11/2004 | Canham |
| 2004/0236271 A1 | 11/2004 | Theeuwes et al. |
| 2004/0265365 A1 | 12/2004 | Daddona et al. |
| 2005/0049549 A1 | 3/2005 | Wong et al. |
| 2005/0065463 A1 | 3/2005 | Tobinaga et al. |
| 2005/0089554 A1 | 4/2005 | Cormier et al. |
| 2005/0090803 A1 | 4/2005 | Sherman et al. |
| 2005/0096586 A1 | 5/2005 | Trautman et al. |
| 2005/0163827 A1 | 7/2005 | Zech et al. |
| 2005/0178760 A1 | 8/2005 | Chang et al. |
| 2005/0197308 A1 | 9/2005 | Dalton |
| 2005/0209565 A1 | 9/2005 | Yuzhakov et al. |
| 2005/0228340 A1 | 10/2005 | Cleary et al. |
| 2005/0256045 A1 | 11/2005 | Ameri et al. |
| 2005/0261631 A1 | 11/2005 | Clarke et al. |
| 2005/0271684 A1 | 12/2005 | Trautman et al. |
| 2006/0024358 A1 | 2/2006 | Santini et al. |
| 2006/0067943 A1 | 3/2006 | Maa et al. |
| 2006/0076718 A1 | 4/2006 | Sherman et al. |
| 2006/0095061 A1 | 5/2006 | Trautman et al. |
| 2006/0108914 A1 | 5/2006 | Young |
| 2006/0129174 A1 | 6/2006 | Gartstein et al. |
| 2006/0134188 A1 | 6/2006 | Podhaisky et al. |
| 2006/0149297 A1 | 7/2006 | Sherman et al. |
| 2006/0253079 A1 | 11/2006 | McDonough et al. |
| 2007/0027427 A1 | 2/2007 | Trautman et al. |
| 2007/0191761 A1 | 8/2007 | Boone et al. |
| 2007/0255251 A1 | 11/2007 | Panchula et al. |
| 2008/0009811 A1 | 1/2008 | Cantor |
| 2008/0009825 A1 | 1/2008 | Ringsred et al. |
| 2008/0039805 A1 | 2/2008 | Frederickson et al. |
| 2008/0114298 A1 | 5/2008 | Cantor et al. |
| 2008/0125743 A1 | 5/2008 | Yuzhakov |
| 2008/0183144 A1 | 7/2008 | Trautman et al. |
| 2008/0188771 A1 | 8/2008 | Boecker et al. |
| 2008/0195035 A1 | 8/2008 | Fredrickson et al. |
| 2008/0208134 A1 | 8/2008 | Tomono |
| 2008/0208146 A1 | 8/2008 | Brandwein et al. |
| 2008/0214987 A1 | 9/2008 | Xu |
| 2008/0221532 A1 | 9/2008 | Ogawa |
| 2008/0269685 A1 | 10/2008 | Singh et al. |
| 2009/0017210 A1 | 1/2009 | Andrianov et al. |
| 2009/0035446 A1 | 2/2009 | Kwon |
| 2009/0041810 A1 | 2/2009 | Andrianov et al. |
| 2009/0043279 A1 | 2/2009 | Kaspar et al. |
| 2009/0155330 A1 | 6/2009 | Ghartey-Tagoe et al. |
| 2009/0182306 A1 | 7/2009 | Lee et al. |
| 2009/0216215 A1 | 8/2009 | Thalmann et al. |
| 2010/0028390 A1 | 2/2010 | Cleary et al. |
| 2010/0200494 A1 | 8/2010 | Storer |
| 2010/0228203 A1 | 9/2010 | Quan et al. |
| 2010/0247698 A1 | 9/2010 | Zhang et al. |
| 2011/0006458 A1 | 1/2011 | Sagi et al. |
| 2011/0028905 A1 | 2/2011 | Takada |
| 2011/0046638 A1 | 2/2011 | Gartstein et al. |
| 2011/0059150 A1 | 3/2011 | Kendall et al. |
| 2011/0098651 A1 | 4/2011 | Falo et al. |
| 2011/0121486 A1 | 5/2011 | Oh et al. |
| 2011/0160069 A1 | 6/2011 | Corrie et al. |
| 2011/0165236 A1 | 7/2011 | Chow et al. |
| 2011/0177139 A1 | 7/2011 | Hyungil et al. |
| 2011/0276027 A1 | 11/2011 | Trautman et al. |
| 2011/0276028 A1 | 11/2011 | Singh et al. |
| 2011/0280800 A1 | 11/2011 | Wu et al. |
| 2011/0288484 A1 | 11/2011 | Kendall et al. |
| 2011/0288485 A1 | 11/2011 | Tokumoto et al. |
| 2011/0295205 A1 | 12/2011 | Kaufmann et al. |
| 2011/0306853 A1 | 12/2011 | Black et al. |
| 2012/0052120 A1 | 3/2012 | Castor |
| 2012/0123297 A1 | 5/2012 | Brancazio |
| 2012/0123387 A1 | 5/2012 | Gonzalez et al. |
| 2012/0126297 A1 | 5/2012 | Brancazio |
| 2012/0130306 A1 | 5/2012 | Terahara et al. |
| 2012/0150023 A1 | 6/2012 | Kaspar et al. |
| 2012/0184906 A1 | 7/2012 | McAllister |
| 2012/0330250 A1 | 12/2012 | Kuwahara et al. |
| 2013/0131598 A1 | 5/2013 | Trautman et al. |
| 2013/0150822 A1 | 6/2013 | Ross |
| 2013/0287832 A1 | 10/2013 | O'Hagan et al. |
| 2013/0292868 A1 | 11/2013 | Singh et al. |
| 2013/0292886 A1 | 11/2013 | Sagi et al. |
| 2013/0303502 A1 | 11/2013 | Cavanagh et al. |
| 2014/0148846 A1 | 5/2014 | Pereira et al. |
| 2014/0180201 A1 | 6/2014 | Ding et al. |
| 2014/0248312 A1 | 9/2014 | Rappuoli et al. |
| 2014/0257188 A1 | 9/2014 | Kendall et al. |
| 2014/0272101 A1 | 9/2014 | Chen et al. |
| 2014/0276366 A1 | 9/2014 | Bourne et al. |
| 2014/0276378 A1 | 9/2014 | Chen et al. |
| 2014/0276474 A1 | 9/2014 | Ding et al. |
| 2014/0276580 A1 | 9/2014 | Le et al. |
| 2014/0276589 A1 | 9/2014 | Bayramov et al. |
| 2014/0330198 A1 | 11/2014 | Zhang et al. |
| 2015/0079133 A1 | 3/2015 | Ghartey-Tagoe et al. |
| 2015/0238413 A1 | 8/2015 | Mochizuki et al. |
| 2015/0297878 A1 | 10/2015 | Singh et al. |
| 2016/0058992 A1 | 3/2016 | Chen et al. |
| 2016/0067176 A1 | 3/2016 | Ding et al. |
| 2016/0135895 A1 | 5/2016 | Faasse et al. |
| 2016/0175572 A1 | 6/2016 | Crowley et al. |
| 2016/0374939 A1 | 12/2016 | Shastry et al. |
| 2017/0050010 A1 | 2/2017 | Mcallister et al. |
| 2017/0281535 A1 | 10/2017 | Singh et al. |
| 2017/0361079 A1 | 12/2017 | Trautman et al. |

FOREIGN PATENT DOCUMENTS

| | | |
|---|---|---|
| CA | 2316534 | 3/2001 |
| CA | 2422907 | 4/2002 |
| CA | 2889500 A1 | 5/2014 |
| CN | 102000020 A | 6/2011 |
| CN | 102580232 A | 7/2012 |
| DE | 02319591 | 11/1974 |
| DE | 19518974 | 11/1995 |
| DE | 19624578 | 1/1998 |
| EP | 0156471 | 10/1985 |
| EP | 0240593 | 10/1987 |
| EP | 0301599 | 2/1989 |
| EP | 0305123 A1 | 3/1989 |
| EP | 0312662 | 4/1989 |
| EP | 0400249 | 12/1990 |
| EP | 0407063 | 1/1991 |
| EP | 0796128 | 9/1997 |

(56) References Cited

FOREIGN PATENT DOCUMENTS

| | | |
|---|---|---|
| EP | 1086718 A1 | 3/2001 |
| EP | 1086719 A1 | 3/2001 |
| EP | 1174078 | 1/2002 |
| EP | 2283809 A1 | 2/2011 |
| EP | 2399624 A1 | 12/2011 |
| FR | 2535602 | 5/1984 |
| GB | 0783479 | 9/1957 |
| GB | 2221394 | 2/1990 |
| GB | 2277202 | 10/1994 |
| JP | 46-037758 | 12/1971 |
| JP | 60-242042 | 12/1985 |
| JP | 62-213763 | 9/1987 |
| JP | 01-264839 | 10/1989 |
| JP | 02-009755 | 3/1990 |
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-146777 | 5/2000 |
| JP | 2000-147229 | 5/2000 |
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |
| JP | 2001-004442 | 1/2001 |
| JP | 2001-138300 | 5/2001 |
| JP | 2001-149485 A | 6/2001 |
| JP | 2001-157715 | 6/2001 |
| JP | 2001-341314 | 12/2001 |
| JP | 2002-000728 A | 1/2002 |
| JP | 2002-079499 | 3/2002 |
| JP | 2002-151395 | 5/2002 |
| JP | 2002-239014 | 8/2002 |
| JP | 2002-301698 | 10/2002 |
| JP | 2003-039399 | 2/2003 |
| JP | 2003-048160 | 2/2003 |
| JP | 2003-534881 A | 11/2003 |
| JP | 2004-065775 A | 3/2004 |
| JP | 2006-271781 A | 10/2006 |
| JP | 2006-341089 A | 12/2006 |
| JP | 2007-130030 A | 5/2007 |
| JP | 2007-190112 A | 8/2007 |
| JP | 2007-536988 A | 12/2007 |
| JP | 2008-006178 A | 1/2008 |
| JP | 2008-074763 A | 4/2008 |
| JP | 2008-194288 A | 8/2008 |
| JP | 2009-082206 A | 4/2009 |
| JP | 2009-082207 A | 4/2009 |
| JP | 2009-201956 A | 9/2009 |
| JP | 2010-233673 A | 10/2010 |
| JP | 2010-233674 A | 10/2010 |
| KR | 20100064669 A | 6/2010 |
| RU | 2414255 C1 | 3/2011 |
| SU | 1641346 | 4/1991 |
| SU | 1667864 | 8/1991 |
| WO | WO 1993/015701 | 8/1993 |
| WO | WO 1993/017754 | 9/1993 |
| WO | WO 1994/023777 | 10/1994 |
| WO | WO 1995/022612 | 8/1995 |
| WO | WO 1995/033612 | 12/1995 |
| WO | WO 1996/000109 | 1/1996 |
| WO | WO 1996/017648 | 6/1996 |
| WO | WO 1996/037155 | 11/1996 |
| WO | WO 1996/037256 | 11/1996 |
| WO | WO 1997/003629 | 2/1997 |
| WO | WO 1997/003718 | 2/1997 |
| WO | WO 1997/013544 | 4/1997 |
| WO | WO 1997/048440 | 12/1997 |
| WO | WO 1997/048441 | 12/1997 |
| WO | WO 1997/048442 | 12/1997 |
| WO | WO 1998/000193 | 1/1998 |
| WO | WO 1998/028307 | 7/1998 |
| WO | WO 1999/000155 | 1/1999 |
| WO | WO 1999/029298 | 6/1999 |
| WO | WO 1999/029364 | 6/1999 |
| WO | WO 1999/029365 | 6/1999 |
| WO | WO 1999/049874 A1 | 10/1999 |
| WO | WO 1999/061888 | 12/1999 |
| WO | WO 1999/064580 | 12/1999 |
| WO | WO 2000/005166 | 2/2000 |
| WO | WO 2003/026733 A2 | 4/2000 |
| WO | WO 2000/035530 | 6/2000 |
| WO | WO 2000/070406 | 11/2000 |
| WO | WO 2000/074763 A2 | 12/2000 |
| WO | WO 2000/074764 | 12/2000 |
| WO | WO 2000/074765 | 12/2000 |
| WO | WO 2000/074766 | 12/2000 |
| WO | WO 2000/077571 | 12/2000 |
| WO | WO 2001/008242 | 2/2001 |
| WO | WO 2001/036037 | 5/2001 |
| WO | WO 2001/036321 | 5/2001 |
| WO | WO 2001/049362 | 7/2001 |
| WO | WO 2002/002180 | 1/2002 |
| WO | WO 2002/007543 | 1/2002 |
| WO | WO 2002/007813 | 1/2002 |
| WO | WO 2002/017985 | 3/2002 |
| WO | WO 2002/030301 A1 | 4/2002 |
| WO | WO 2002/032331 | 4/2002 |
| WO | WO 2002/032480 | 4/2002 |
| WO | WO 2002/062202 | 8/2002 |
| WO | WO 2002/064193 A2 | 8/2002 |
| WO | WO 2002/072189 | 9/2002 |
| WO | WO 2002/085446 A2 | 10/2002 |
| WO | WO 2002/091922 | 11/2002 |
| WO | WO 2002/100474 | 12/2002 |
| WO | WO 2003/024290 | 3/2003 |
| WO | WO 2003/024518 | 3/2003 |
| WO | WO 2004/000389 A2 | 12/2003 |
| WO | WO 2004/009172 A1 | 1/2004 |
| WO | WO 2004/024224 A1 | 3/2004 |
| WO | WO 2004/030649 A2 | 4/2004 |
| WO | WO 2004/076339 | 9/2004 |
| WO | WO 2004/105729 A2 | 12/2004 |
| WO | WO 2004/110717 | 12/2004 |
| WO | WO 2005/002453 A1 | 1/2005 |
| WO | WO 2005/046769 A2 | 5/2005 |
| WO | WO 2005/065765 A1 | 7/2005 |
| WO | WO 2005/082596 A1 | 9/2005 |
| WO | WO 2005/089857 A1 | 9/2005 |
| WO | WO 2005/094526 | 10/2005 |
| WO | WO 2005/099751 A2 | 10/2005 |
| WO | WO 2005/112984 A2 | 12/2005 |
| WO | WO 2006/020842 | 2/2006 |
| WO | WO 2006/055795 | 5/2006 |
| WO | WO 2006/062848 A1 | 6/2006 |
| WO | WO 2006/086742 A2 | 8/2006 |
| WO | WO 2006/101459 A1 | 9/2006 |
| WO | WO 2007/002521 A2 | 1/2007 |
| WO | WO 2007/002522 A1 | 1/2007 |
| WO | WO 2007/002523 | 1/2007 |
| WO | WO 2007/012114 A1 | 2/2007 |
| WO | WO 2007/030477 A2 | 3/2007 |
| WO | WO 2007/061964 A1 | 5/2007 |
| WO | WO 2007/061972 A2 | 5/2007 |
| WO | WO 2007/075806 A2 | 7/2007 |
| WO | WO 2007/081430 A2 | 7/2007 |
| WO | WO 2007/124411 | 11/2007 |
| WO | WO 2008/011625 | 1/2008 |
| WO | WO 2008/015236 A1 | 2/2008 |
| WO | WO 2008/024141 A2 | 2/2008 |
| WO | WO 2008/091602 | 7/2008 |
| WO | WO 2008/130587 | 10/2008 |
| WO | WO 2008/139648 A1 | 11/2008 |

(56) References Cited

FOREIGN PATENT DOCUMENTS

| | | |
|---|---|---|
| WO | WO 2009/039013 A1 | 3/2009 |
| WO | WO 2009/048607 A1 | 4/2009 |
| WO | WO 2009/054988 A1 | 4/2009 |
| WO | WO 2009/142741 A1 | 11/2009 |
| WO | WO 2010/040271 A1 | 4/2010 |
| WO | WO 2010/124255 A2 | 10/2010 |
| WO | WO 2011/121023 A1 | 10/2011 |
| WO | WO 2011/140240 | 10/2011 |
| WO | WO 2011/140274 | 10/2011 |
| WO | WO 2012/054582 A2 | 4/2012 |
| WO | WO 2012/122163 A1 | 9/2012 |
| WO | WO 2012/127249 A1 | 9/2012 |
| WO | WO 2012/153266 A2 | 11/2012 |
| WO | WO 2013/172999 A1 | 11/2013 |
| WO | WO 2014/004301 A1 | 1/2014 |
| WO | WO 2014/077244 A1 | 5/2014 |
| WO | WO 2014/100750 A1 | 6/2014 |
| WO | WO 2014/144973 A1 | 9/2014 |
| WO | WO 2014/150069 A1 | 9/2014 |
| WO | WO 2014/150285 A2 | 9/2014 |
| WO | WO 2014/151654 A1 | 9/2014 |
| WO | WO 2014/164314 A1 | 10/2014 |
| WO | WO 2016/033540 A1 | 3/2016 |
| WO | WO 2016/036866 A1 | 3/2016 |
| WO | WO 2016/073908 A1 | 5/2016 |
| WO | WO 2017/004067 A1 | 1/2017 |

OTHER PUBLICATIONS

Chun, et al., "An array of hollow microcapillaries for the controlled injection of genetic materials into animal/plant cells," IEEE Workshop on Micro Electro Mechanical Systems, pp. 406-411, (1999).
"Extend", Merriam-Webster Online Dictionary, 6 pages, Downloaded on Sep. 7, 2010 from <http://www.merriam-webster.com/dictionary/extend>.
"Extend", Macmillan Online Dictionary, 5 pages, Downloaded on Sep. 7, 2010 from <http://www.macmillandictionary.com/dictionary/american/extend>.
Henry, et al., "Micromachined microneedles for transdermal delivery of drugs", IEEE Workshop on Micro Electro Mechanical Systems, New York, NY, pp. 494-498, (1998).
Henry, et al., "Microfabricated microneedles: A novel approach to transdermal drug delivery", J. Pharmaceutical Science, vol. 87, No. 8, pp. 922-925, (1998).
"Heparin Pregnancy and Breast Feeding Warnings", Drugs.com, Accessed Oct. 8, 2009, <http://www.drugs.com/pregnancy/heparin.html>.
International Search Report from International Patent Application No. PCT/US2000/015612 dated Sep. 7, 2000.
International Search Report from International Patent Application No. PCT/US2000/015613 dated Sep. 6, 2000.
International Search Report from International Patent Application No. PCT/US2000/015614 dated Sep. 6, 2000.
International Search Report from International Patent Application No. PCT/US2001/031977 dated Apr. 29, 2002.
International Search Report from International Patent Application No. PCT/US2001/031978 dated Apr. 29, 2002.
International Search Report from International Patent Application No. PCT/US2002/014624 dated Sep. 3, 2002.
International Search Report from International Patent Application No. PCT/US2002/029228 dated Apr. 23, 2003.
International Search Report from International Patent Application No. PCT/US2002/029245 dated Dec. 27, 2002.
International Search Report from International Patent Application No. PCT/US2004/005382 dated Nov. 25, 2004.
International Search Report from International Patent Application No. PCT/US2004/017255 dated May 24, 2005.
International Search Report from International Patent Application No. PCT/US2005/009854 dated Jul. 3, 2008.
International Search Report from International Patent Application No. PCT/US2008/000824 dated Jul. 18, 2008.
International Search Report from International Patent Application No. PCT/US2008/004943 dated Jun. 9, 2009, application now published as International Publication No. WO2008/130587 Oct. 30, 2008.
International Search Report from International Patent Application No. PCT/US2008/011635 dated Dec. 19, 2008, application now published as International Publication No. WO2009/048607 on Apr. 16, 2009.
International Search Report from International Patent Application No. PCT/US2010/032299 dated Dec. 10, 2010, application now published as International Publication No. WO2010/124255 on Oct. 28, 2010.
International Search Report from International Patent Application No. PCT/US2013/077281 dated Mar. 4, 2013.
International Search Report from International Patent Application No. PCT/US2014/021841 dated Aug. 11, 2014.
International Search Report from International Patent Application No. PCT/US2014/022087 dated May 23, 2014.
International Search Report from International Patent Application No. PCT/US2014/022836 dated May 9, 2015.
International Search Report from International Patent Application No. PCT/US2014/022859 dated May 26, 2014.
International Search Report from International Patent Application No. PCT/US2014/026179 dated Jul. 18, 2014.
International Search Report from International Patent Application No. PCT/US2014/029601 dated Jul. 1, 2014.
Matriano, et al., "Macroflux(R) microprojection array patch technology: A new and efficient approach for intracutaneous immunization", Pharm. Res., vol. 19, No. 1, pp. 63-70, (2002).
McAllister, et al., "Micromachined microneedles for transdermal drug delivery", Am. Inst. Chem. Eng., 1998 Annual Meeting, Miami Beach, FL, Nov. 15-20, Drug Delivery II, pp. 1-4.
Mikszta, et al., "Improved genetic immunization via micromechanical disruption of skin-barrier function and targeted epidermal delivery", Nat. Med., vol. 8, No. 4, pp. 415-419, (2002).
Mikszta, et al., "Protective immunization against inhalation anthrax: A comparison of minimally invasive delivery platforms", J. Inf. Dis., vol. 191, No. 2, pp. 278-288, (2005).
Papautsky, et al., "Micromachined Pipette Arrays," MPA, Proceedings—19th international Conference—IEEE/EMBS, Chicago IL, USA, pp. 2281-2284 (1997).
Park et al., "Biodegradable polymer microneedles: Fabrication, mechanics, and transdermal drug delivery", J. Contr. Rel., vol. 104, pp. 51-66 (2005).
Park, et al. "Polymer Microneedles for Controlled-Release Drug Delivery," Pharmaceutical Research, Kluwer Academic Publishers-Plenum Publishers, NE, vol. 23, No. 5, pp. 1008-1019 (2006).
Prausnitz, et al., "Transdermal transport efficiency during skin electroporation and iontophoresis", J. Contr. Release, vol. 38, pp. 205-217, (1996).
Prausnitz, "Transdermal delivery of macromolecules: Recent advances by modification of skin's barrier properties", ACS Symposium Series No. 675, *Therapeutic Protein and Peptide Formulation and Delivery*, American Chemical Society, Washington DC, Chapter 8, pp. 124-153, (1997).
Rydberg, et al., "Low-molecular-weight heparin preventing and treating DVT", Am. Fam. Physician, vol. 59, No. 6, pp. 1607-1612, (1999).
Sivamani, et al., "Microneedles and transdermal applications", Exp. Opin. Drug Del., vol. 4, No. 1, pp. 19-25, (2007).
Wouters, et al., "Microelectrochemical systems for drug delivery", Electrochimica Acta., vol. 42, pp. 3385-3390, (1997).
Xia, et al., "Soft Lithography", Angew. Chem. Int. Ed., vol. 37, pp. 551-575, (1998).
Xia, et al., "Soft Lithography", Annu. Rev. Mater. Sci., vol. 28, pp. 153-184 (1998).
International Search Report from International Patent Application No. PCT/US2011/035221 dated Jan. 10, 2012, application now published as International Publication No. WO2011/140240 on Nov. 10, 2011.

(56) References Cited

OTHER PUBLICATIONS

International Search Report from International Patent Application No. PCT/US2015/059559 dated Jan. 21, 2016.
International Search Report from International Patent Application No. PCT/US2016/039864 dated Sep. 23, 2016.
Keitel et al., "A randomized clinical trail of acellular pertussis vaccines in healthy adults: Dose-response comparisons of 5 vaccines and implications for booster immunization", J. Infect. Dis., vol. 180, pp. 397-403 (1999).
Lutrol F 68 NF, BASF Pharma Ingredients, accessed from the internet on Sep. 5, 2016 from http://www2.basf.us/Pharma/pdf/Lutrol_F_68.pdf.
Makaida et al., "Poly lactic-co-glycolic acid (PLGA) as biodegradable controlled drug delivery carrier", Polymers (Basel), vol. 3, No. 3, pp. 1377-1397 (2011).
Vitiello et al., "Development of a lipopeptide-based therapeutic vaccine to treat chronic HBV infection", J. Clin. Invest., vol. 95, pp. 341-349 (1995).
Avcin et al., "Subcutaneous nodule after vaccination with an aluminum-containing vaccina", Acta Dermatoven, APA, vol. 17, No. 4, pp. 182-184 (2008).
Corbett et al., "Skin vaccination against cervical cancer associated human papillomavirus with a novel micro-projection array in a mouse model", PLOS one, vol. 5, No. 10, pp. 1-9 (2010).
Database WPI / Thomson, Accession No. 2014-V8921.8, Gao et al., "Soluble microneedle patch useful for transdermal administration of vaccine, comprises water-soluble polymer material as matrix material and soluble microneedle main portion". Application No. CN104027324A, Tech Inst Phys. & Chem. Chinese Acad., 3 pages (2014).
Ghosh et al., "Influence of critical parameters of nanosuspension formulation on permeability of a poorly soluble drug through the skin—A case study", vol. 14, No. 3, pp. 1108-1117 (2013).
Guo et al., "Enhanced transcutaneous immunization via dissolving microneedle array loaded with liposome encapsulated antigen and adjuvant", Int. J. Pharm., vol. 447, No. 1-2, pp. 22-30 (2013).
Gupta, "Aluminum compounds as vaccine adjuvants", Adv. Drug Deliv. Rev., vol. 32, No. 3, pp. 155-172 (1998) Abstract Only.
Gupta and Rost, "Aluminum compounds as vaccine adjuvants", Vaccine adjuvants: Preparation Methods and Research Protocols, O'Hagan, ed., Humana Press, Inc., Totowa, New Jersey, Meth. Mol. Med., vol. 42, No. 4, No. 4, pp. 65-89 (2000).
International Search Report from International Patent Application No. PCT/US2015/047563 dated Nov. 20, 2015.
International Search Report from International Patent Application No. PCT/US2015/048161 dated Nov. 26, 2015.
Kuroda et al., "Particulate adjuvant and innate immunity: past achievements, present findings, and future prospects", Int. Rev. Immunol., vol. 32, No. 2, pp. 209-220 (2013).
Munks et al., "Aluminum adjuvants elicit fibrin-dependent extracellular traps in vivo", Blood, vol. 116, No. 24, pp. 5191-5199 (2010).
Petrovsky and Aguilar, "Vaccine adjuvants: current state and future trends", Immunol. Cell Biol., vol. 82, No. 5, pp. 488-496 (2004).
Pittman, "Aluminum-containing vaccine associated adverse events: role of route of administration and gender", Vaccine, vol. 20, pp. s48-s50 (2002).
Prausnitz, "Microneedle-based vaccines", Curr. Top. Microbiol. Immunol., vol. 333, pp. 369-393 (2009).
Sayers et al., "Vaxjo: A Web-Based Vaccine Adjuvant Database and Its Application for Analysis of Vaccine Adjuvants and Their Uses in Vaccine Development", J. Biomed. Biotechnol., vol. 2012, Article ID: 831486, 13 pages, doi:10.1155/2012/831486 (2011).
White et al., "Studies on antibody production. III. The alum granuloma:", J. Exp. Med., vol. 102, No, 1, pp. 73-82 (1955).
Julinova et al., "Initiating biodegradation of polyvinylpyrrolidone in aqueous aerobic environment", Proceedings of ECOpole, vol. 6, No. 1, pp. 121-127 (2012).
Kunduru et al., "Biodegradable polymers: Medical Applications", Encyclopedia of Polymer Science and Technology, pp. 1-22 (2016) DOI: 10.1002/0471440264.pst027.pub2.
Polysorbate 80, Material Safety Data Sheet, CAS#: 9005-65-6, Science Lab.com, Inc., 14025 Smith Rd., Houston, Texas 77396, 5 pages, Last updated May 21, 2013.

SOLVENT-CAST MICROPROTRUSION ARRAYS CONTAINING ACTIVE INGREDIENT

CROSS-REFERENCE TO RELATED APPLICATIONS

This application is a continuation of U.S. application Ser. No. 12/148,180, filed Apr. 16, 2008, now U.S. Pat. No. 9,114,238, which claims priority to U.S. Provisional Application No. 60/925,262, filed Apr. 18, 2007, and U.S. Provisional Application No. 60/923,861, filed Apr. 16, 2007, each of which is incorporated by reference herein in its entirety.

TECHNICAL FIELD

This invention relates generally to drug delivery using microneedles or other microprojections.

BACKGROUND

Arrays of microneedles were proposed as a way of administering drugs through the skin in the 1970s, for example in expired U.S. Pat. No. 3,964,482. Microneedle arrays can facilitate the passage of drugs through or into human skin and other biological membranes in circumstances where ordinary transdermal administration is inadequate. Microneedle arrays can also be used to sample fluids found in the vicinity of a biological membrane such as interstitial fluid, which is then tested for the presence of biomarkers.

In recent years it has become more feasible to manufacture microneedle arrays in a way that makes their widespread use financially feasible. U.S. Pat. No. 6,451,240 discloses some methods of manufacturing microneedle arrays. If the arrays are sufficiently inexpensive, for example, they may be marketed as disposable devices. A disposable device may be preferable to a reusable one in order to avoid the question of the integrity of the device being compromised by previous use and to avoid the potential need of resterilizing the device after each use and maintaining it in controlled storage.

Despite much initial work on fabricating microneedle arrays in silicon or metals, there are significant advantages to polymeric arrays. U.S. Pat. No. 6,451,240 discloses some methods of manufacturing polymeric microneedle arrays. Arrays made primarily of biodegradable polymers have some advantages. U.S. Pat. No. 6,945,952 and U.S. Published Patent Applications Nos. 2002/0082543 and 2005/0197308 have some discussion of microneedle arrays made of biodegradable polymers. A detailed description of the fabrication of a microneedle array made of polyglycolic acid is found in Jung-Hwan Park et al., "Biodegradable polymer microneedles: Fabrication, mechanics, and transdermal drug delivery," *J. of Controlled Release*, 104:51-66 (2005).

Despite these efforts, there is still a need to find simpler and better methods for the manufacture of polymeric arrays and in particular arrays made of biodegradable polymers. A particular desideratum is a method which works at a relatively low temperature so that temperature sensitive actives may be delivered by means of such arrays.

SUMMARY OF THE INVENTION

In an aspect of the invention, an array of microprotrusions is provided comprising an approximately planar base and a plurality of microprotrusions, wherein the array comprises a plurality of layers arranged roughly parallel to the plane of the base, at least two of the plurality of layers comprise different polymers, a first layer of the plurality of layers is contained in the microprojections, and optionally at least one layer of the plurality of layers comprises an active ingredient.

In a further aspect of the invention, an array of microprotrusions is formed by (a) providing a mold with cavities corresponding to the negative of the microprotrusions, (b) casting a solution comprising a biocompatible material and a solvent atop the mold, (c) removing the solvent, (d) demolding the resulting array from the mold, and (e) taking at least one measure to avoid the formation or adverse effects of bubbles.

FIGURES

DETAILED DESCRIPTION OF PREFERRED EMBODIMENTS

Before describing the present invention in detail, it is to be understood that this invention is not limited to specific solvents, materials, or device structures, as such may vary. It is also to be understood that the terminology used herein is for the purpose of describing particular embodiments only, and is not intended to be limiting.

As used in this specification and the appended claims, the singular forms "a," "an," and "the" include both singular and plural referents unless the context clearly dictates otherwise. Thus, for example, reference to "an active ingredient" includes a plurality of active ingredients as well as a single active ingredient, reference to "a temperature" includes a plurality of temperatures as well as single temperature, and the like.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also disclosed, as well as the range of values greater than or equal to 1 µm and the range of values less than or equal to 8 µm.

In this application reference is often made for convenience to "skin" as the biological membrane through which the active is administered. It will be understood by persons of skill in the art that in most or all instances the same inventive principles apply to administration through other biological membranes such as those which line the interior of the mouth, gastro-intestinal tract, blood-brain barrier, or other body tissues or organs or biological membranes which are exposed or accessible during surgery or during procedures such as laparoscopy or endoscopy.

In this application reference is also made to "microneedles" as the type of microprotrusion or microprojection which is being employed. It will be understood by persons of skill in the art that in many cases the same inventive principles apply to the use of other microprotrusions or microprojections to penetrate skin or other biological membranes. Other microprotrusions or microprojections may include, for example, microblades as described in U.S. Pat. No. 6,219,574 and Canadian patent application no. 2,226,718, and edged microneedles as described in U.S. Pat. No. 6,652,478.

Figure 4:
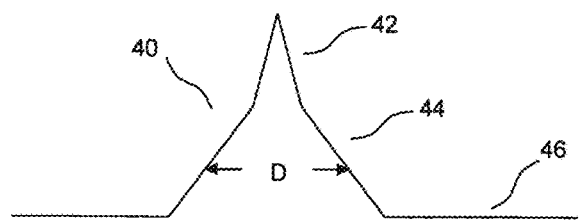
FIG. 4 depicts schematically in cross-section a microprojection in which the diameter of the microprojection decreases more rapidly with distance from the base closer to the base compared to further away from the base.

In general it is preferred that the microprojections have a height of at least about 100 µm, at least about 150 µm, at least about 200 µm, at least about 250 µm, or at least about 300 µm. In general it is also preferred that the microprojections have a height of no more than about 1 mm, no more than about 500 µm, no more than about 300 µm, or in some cases no more than about 200 µm or 150 µm. The microprojections may have an aspect ratio of at least 3:1 (height to diameter at base), at least about 2:1, or at least about 1:1. A particularly preferred shape for the microprojections is a cone with a polygonal bottom, for example hexagonal or rhombus-shaped. Other possible microprojection shapes are shown, for example, in U.S. Published Patent App. 2004/0087992. Microprojections may in some cases have a shape which becomes thicker towards the base, for example microprojections which have roughly the appearance of a funnel, or more generally where the diameter of the microprojection grows faster than linearly with distance to the microprojection's distal end. Such a shape may, for example, facilitate demolding. FIG. 4 schematically depicts in cross-section a microprojection 40 of this type. As may be seen in the figure, the diameter D of the microprojection's intersection with a plane parallel to the base 46 decreases as the plane moves away from the base 46. In addition, this diameter decreases more rapidly close to the base, in zone 44, than it does further away from the base, in zone 42.

Where microprojections are thicker towards the base, a portion of the microprojection adjacent to the base, which we may call "foundation," may be designed not to penetrate the skin.

The number of microprotrusions in the array is preferably at least about 100, at least about 500, at least about 1000, at least about 1400, at least about 1600, or at least about 2000. The area density of microprotrusions, given their small size, may not be particularly high, but for example the number of microprotrusions per $cm^2$ may be at least about 50, at least about 250, at least about 500, at least about 750, at least about 1000, or at least about 1500.

In an aspect of the invention, an array of microprotrusions is formed by (a) providing a mold with cavities corresponding to the negative of the microprotrusions, (b) casting atop the mold a solution comprising a biocompatible material and a solvent, (c) removing the solvent, (d) demolding the resulting array from the mold. The solution preferably contains an active ingredient.

The molds used to form the microneedles in methods of the invention can be made using a variety of methods and materials. In contrast to other methods of making microneedle arrays, for the methods of the invention no particularly high degree of heat resistance is necessarily required of the mold.

The mold may, for example, conveniently comprise a ceramic material. Alternatively, for example, the mold may comprise a silicone rubber or a polyurethane. The mold may alternatively comprise a wax. A particular silicone rubber system which may be used is the Sylgard® system from Dow Corning (Midland, Mich.), for example Sylgard 184. Nusil MED 6215 is an alternative system available from NuSil Technology (Carpinteria, Calif.). The mold may conveniently be made of or comprise a porous material.

There are a number of ways of making the molds. The molds can be made, for example, by casting the liquid mold material over a master microneedle array and allowing the material to dry and harden. In some cases, curing of the material may take place during the drying process. For some materials curing agents may be added. Silicone rubbers and polyurethane are two types of materials that can be used to make molds in this way.

The molds can be made by heating the mold material until it melts. The liquid is then cast over the master microneedle array and allow the material to cool and harden. Waxes and thermoplastics are two classes of materials that can be used to make molds in this way.

The molds can be made by pressing the master microneedle array into the mold material. For this manufacturing technique, the mold material is preferably much softer than the microneedle array. The mold material can be heated to soften it. Waxes and thermoplastics are two types of materials that can be used to make molds in this way.

The molds can be made by plating metal (such as nickel, copper or gold) onto a master microneedle array.

The molds can be made by machining the cavities into the mold material. Electrostatic discharge machining (EDM) can be used to make cavities in metals. Reactive ion etching (RIE) can be used to create the cavities, for example, in silicon and other semiconductors.

The step of casting may be performed by a number of methods known to those of skill in the art. Example 1 describes briefly a way of performing the step of casting. Goals of casting include roughly uniform coverage of the surface of the mold on which the microneedle array is expected to be formed.

The solution which is cast preferably comprises one or more polymers in a solvent and an active ingredient. The polymers should be biocompatible. The polymers are preferably biodegradable. By this term we mean that a polymer will degrade under expected conditions of in vivo use (e.g., insertion into skin), irrespective of the mechanism of biodegradation. Exemplary mechanisms of biodegradation include disintegration, dispersion, dissolution, erosion, hydrolysis, and enzymatic degradation.

For example, suitable biocompatible, biodegradable, or bioerodible polymers include poly(lactic acid) (PLA), poly (glycolic acid) (PGA), poly(lactic acid-co-glycolic acid)s (PLGAs), polyanhydrides, polyorthoesters, polyetheresters, polycaprolactones (PCL), polyesteramides, poly(butyric acid), poly(valeric acid), polyvinylpyrrolidone (PVP), polyvinyl alcohol (PVA), polyethylene glycol (PEG), block copolymers of PEG-PLA, PEG-PLA-PEG, PLA-PEG-PLA, PEG-PLGA, PEG-PLGA-PEG, PLGA-PEG-PLGA, PEG-PCL, PEG-PCL-PEG, PCL-PEG-PCL, copolymers of ethylene glycol-propylene glycol-ethylene glycol (PEG-PPG-PEG, trade name of Pluronic® or Poloxamer®), dextran, hetastarch, tetrastarch, pentastarch, hydroxyethyl starches, cellulose, hydroxypropyl cellulose (HPC), sodium carboxymethyl cellulose (Na CMC), thermosensitive HPMC (hydroxypropyl methyl cellulose), polyphosphazene, hydroxyethyl cellulose (HEC), other polysaccharides, poly-alcohols, gelatin, alginate, chitosan, hyaluronic acid and its derivatives, collagen and its derivatives, polyurethanes, and copolymers and blends of these polymers. A preferred hydroxyethyl starch may have a degree of substitution of in the range of 0-0.9.

The polymers used in the invention may have a variety of molecular weights. The polymers may, for example, have molecular weights of at least about 5 kD, at least about 10 kD, at least about 20 kD, at least about 22 kD, at least about 30 kD, at least about 50 kD, or at least about 100 kD.

Preferred solvents for casting include water, alcohols (for example, $C_2$ to $C_8$ alcohols such as propanol and butanol), and alcohol esters, or mixtures of these. Other possible non-aqueous solvents include esters, ethers, ketones, nitrites, lactones, amides, hydrocarbons and their derivatives as well as mixtures thereof.

In the step of casting the solution on the mold, it is commonly desired to avoid the presence of bubbles of air between the solution and the mold when it is cast. A number of techniques may be employed within the methods of the invention for avoiding these bubbles.

The mold itself, or portions of it, may be subject to surface treatments which make it easier for the solution to wet the mold surface. For example, the mold surface can be coated with a surfactant such as Jet Dry, polysorbate, docusate sodium salt, benzethonium chloride, alkyltrimethylammonium bromide or hexadecyltrimethylammonium bromide (CTAB). Wettability of silicone mold surfaces may be improved by covering them with a solution of hydroxypropylcellulose (HPC) in organic solvent.

The mold surface can be coated with a salt such as calcium carbonate. Calcium carbonate can conveniently be formed in situ from calcium bicarbonate. The mold surface is coated by covering it with a solution containing equivalent quantities of calcium chloride and sodium bicarbonate to form calcium bicarbonate solution in situ. Ultrasonic energy is then applied to precipitate the calcium carbonate salt which is formed as calcium bicarbonate decomposition product under these conditions.

The wettability of the mold surface can also be improved by radiofrequency (RF) or plasma treatment. Alternatively, it is possible to attach to the surface appropriate small molecules, for example in a reaction which is triggered by ultraviolet light. Exemplary small molecules are vinyl monomers comprising carboxyl, primary or secondary or tertiary amine and/or hydroxyl groups, for example acrylic acid, methacrylic acid, allyl amine, or hydroxyethyl methylacrylate (HEMA).

Surface treatments suitable for inducing hydrophilicity are described also in U.S. Published Patent Application No. 20060097361.

A wetting agent, for example Dow Corning Q2-5211, can be added to the mold itself as it is being formed. Q2-5211 is described by Dow Corning as a low molecular weight nonionic silicone polyether surfactant. Being mixed in with the mold as it is formed, the wetting agent becomes part of the mold.

A surfactant such as alkyltrimethylammonium bromide (Cetrimide), hexadecyltrimethylammonium bromide (CTAB), benzethonium chloride, docusate sodium salt, a SPAN-type surfactant, polysorbate (Tween), sodium dodecyl sulfate (SDS), benzalkonium chloride, or glyceryl oleate can be added to the solution.

An anti-foaming agent can be added to the solution. Exemplary antifoaming agents include Dow Corning's FG-10 antifoam Emulsion, Antifoam C Emulsion, 190 fluid, and 193C fluid.

The cavities can be filled with a wetting liquid that easily flows into the cavities and will be absorbed by the mold. The wetting liquid could be ethyl acetate or silicone fluid when the mold is made of silicone rubber. The drug solution is cast over the wetting liquid and is drawn into the cavities as the wetting liquid is absorbed.

The drug solution can be cast onto the mold while a vacuum is applied over the cavities. A low-pressure bubble covered with a liquid film of drug solution can form in the cavities. When the vacuum is removed, the higher pressure over the liquid film will shrink the bubble in the cavity and push the drug solution in behind it.

Alternatively, the mold may be designed to possess a porosity sufficient to allow air to escape from bubbles that may be found between the solution and the mold, but not sufficient for the solution itself to enter the mold's pores.

A further technique which may be employed to avoid air bubbles is to place the mold under compression prior to casting. The compression may be, for example, from two opposite sides. The compression will tend to reduce the volume of the cavities into which the solution must enter. The solution is then cast on the compressed mold. The compression is then released. Upon releasing the compression, the solution is drawn into the cavities as they expand to their normal volume. This process can be performed across the entire mold simultaneously or can be performed on sections of the mold.

The step of casting may alternatively be carried out under an atmosphere which passes more readily through the solution than air would, for example carbon dioxide or another gas whose solubility is greater than that of nitrogen or oxygen, the major constituents of air.

If a bubble is not prevented from forming in a cavity, several methods can be used to remove the bubble. For example, the bubble may be dislodged by vibrating the mold with the drug solution on it.

Pressurization of the cast solution and mold may help eliminate bubbles. In general, the gas in a bubble is expected to diffuse into the liquid over a period of time. When this happens, drug solution is expected to flow into the cavity due to gravitational pull and hydrostatic pressure. The filling and diffusion processes can be accelerated by pressurization. Drying of the liquid is preferably slowed during this period so the liquid can flow into the cavity as the gas from the bubble diffuses into the liquid. Pressurization can be accomplished by placing the mold with the drug solution on it into a pressure vessel. Pressurization may involve a pressure of at least about 3 psi, about 5 psi, about 10 psi, about 14.7 psi, or about 20 psi above atmospheric.

The Epstein-Plesset equation for the time to the dissolution of a bubble in a liquid gives at least a qualitative understanding of the bubble dissolution taking place when the mold and cast solution are pressurized. However, generally the bubbles in mold cavities will have roughly a conical shape and the bubbles hypothesized by Epstein and Plesset were spherical.

Thus, for example, an exemplary method of casting dispenses the solution on the mold over the cavities. A vacuum is applied, causing air trapped in cavities to expand. The air bubbles flow towards the surface of the solution, which in turn flows down into the cavities. When the pressure is returned to atmospheric, the expanded air left in the cavities compresses down.

Another exemplary method of casting dispenses the solution on the mold over the cavities. An overpressure is applied, for example about 0.5 atmospheres, about 1 atmosphere, or about 1.5 atmospheres, causing air bubbles trapped in cavities to contract. The higher pressure causes the air trapped in the bubbles to dissolve into the liquid and causes the bubbles eventually to disappear. After a suitable time the overpressure can be removed. In order to prevent the formulation from drying during this process, the environment surrounding the mold can be humidified.

A vacuum can be applied after the drug solution is cast over the cavities to make the bubbles expand which increases the force pushing them up through the drug solution. The bubbles then rise to the surface of the liquid and the liquid fills the cavities. Drying of the liquid is preferably slowed during this period so the liquid can flow into the cavity as the bubble rises.

It is possible to combine many of the bubble prevention or elimination methods which are listed above.

During the process of solvent removal, the volume of the cast solution will naturally diminish. With an appropriate choice of solvents, it is possible for the distal ends of the microprojections—those furthest from the base—to become finer as a result of solvent removal. Fineness in these tips may be favorable, all else being equal, for easier penetration of the skin, and may thus be desired. A tip diameter of less than about 10 μm, 5 μm or 2 μm is desirable. A tip diameter of less than about 1.5 μm is desirable, as is a tip diameter of less than about 1 μm.

The solvent removal may be accomplished, for example, by heat, vacuum, or convection. The solvent removal may be assisted by covering the cast solution with an absorbent material.

Particularly where the active ingredient is macromolecular, it is desirable to avoid extensive use of heat in the solvent removal step because of the possibility of irreversible denaturation of the active. For example, it is preferable if no temperature above about 100° C. is used (except perhaps for a brief period), more preferably no temperature above about 90° C., and more preferably no temperature above about 85° C. or 80° C. is employed. More preferably, no temperature above about 50° C., 40° C. or 37° C. is employed.

Cast microprojection arrays may be removed from the mold by using a de-mold tool which has a rolling angle of about 1-90 degrees from the plane. A double-sided adhesive is placed on the back of microprojection array with one side for adhering to the array and the other side for adhering to the de-mold tool. The array is removed from the mold by gently rolling the de-mold tool over the adhesive on the back of the array with a slight the rolling angle, such as about 1-90 degrees, preferred about 5-75 degrees, more preferred about 10-45 degrees. The microprojection array is then gently peeled off from the de-mold tool.

In an aspect of the invention, an array of microprotrusions is provided comprising an approximately planar base and a plurality of microprotrusions, wherein the array comprises a plurality of layers arranged roughly parallel to the plane of the base, at least two of the plurality of layers comprise different polymers, and optionally at least one layer of the plurality of layers comprises an active ingredient.

Arrays of the invention may be designed, for example, such that at least one layer of the array adheres to human skin.

There are a number of reasons why arrays with multiple layers may be desirable. For example, it is often desirable that, compared to the whole volume of the microprojection array, the microprojections themselves have a higher concentration of active ingredient. This is so, for example, because the microprojections can be expected in many cases to dissolve more rapidly, being more hydrated than the base of the array. Furthermore, in some protocols for array application, the array may be left in for a short period of time during which essentially only the microprojections can dissolve to a substantial extent. The desirability of placing a higher concentration of active in the projections themselves is particularly acute when the active is costly. A way to achieving a higher concentration of active in the projections themselves is to have a first layer which includes the microprojections or a substantial proportion of the microprojections, and a second layer which includes the base or a substantial proportion of the base.

Figure 5A:
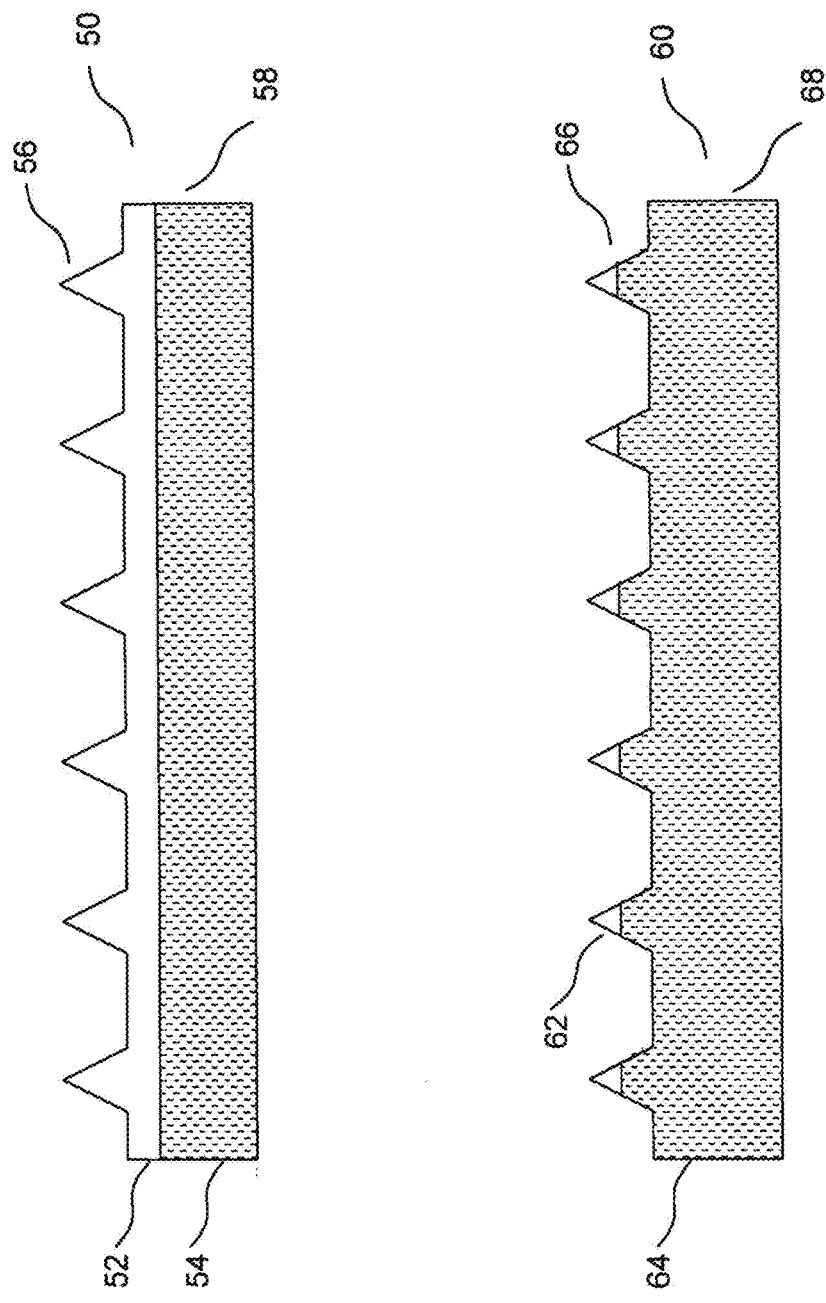
FIGS. 5A-5C depict schematically in cross-section five exemplary types of microprojection arrays of the invention.

FIG. 5A depicts schematically in cross-section two exemplary microprojection arrays of the invention. In the first microprojection array 50, there is a base 58 and a plurality of microprojections such as 56. The microprojection array comprises two layers 52 and 54 (shaded). As may be seen, the microprojections themselves fall entirely within layer 52, so that layer 54 does not contain any microprojections. In the second microprojection array 60, there are also a plurality of microprojections such as 66. The microprojection array comprises two layers 62 and 64 (shaded). However, in array 60 the layer 62 encompasses only a portion of the microprojections which comprises their tips or distal ends. The layer 64 encompasses the portion of the microprojections not contained in layer 62 and also encompasses the totality of the base 68.

Figure 5B:
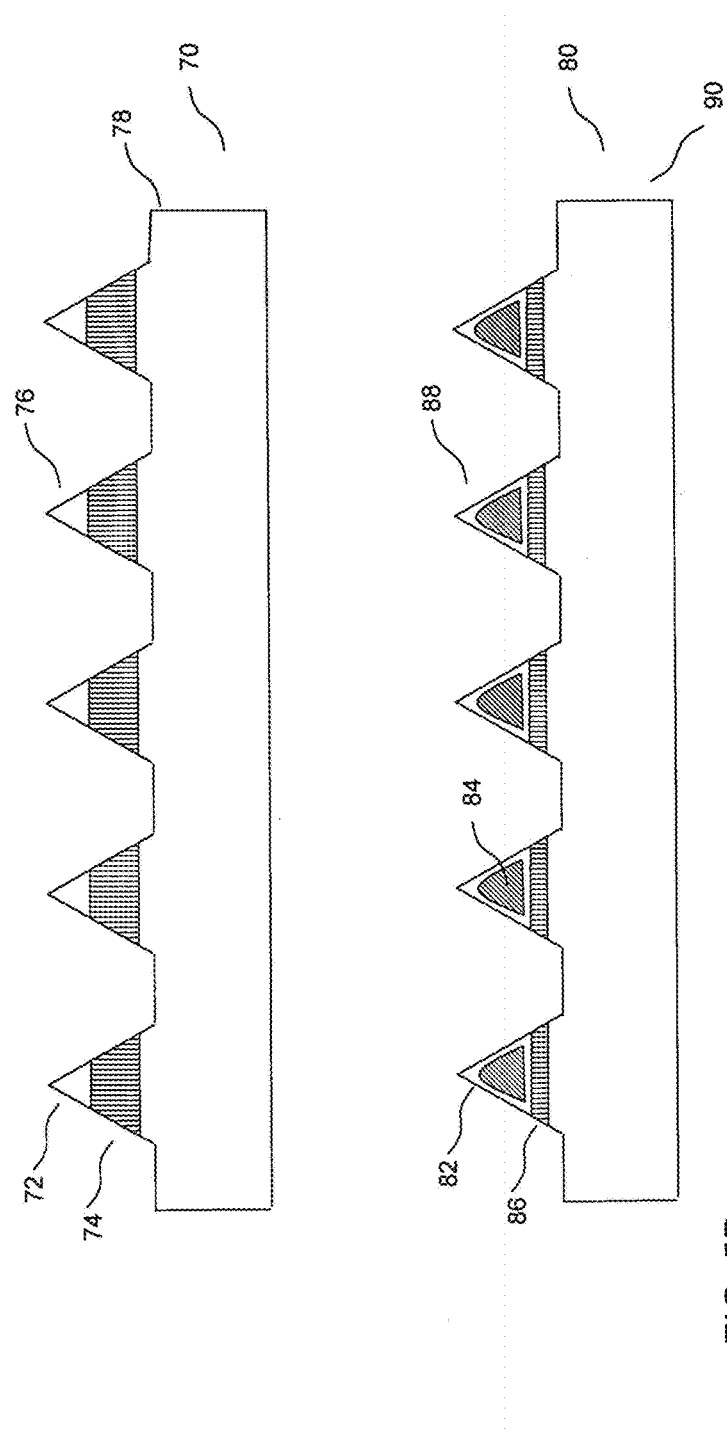

FIG. 5B depicts two further types of microprojection arrays schematically in cross-section. In microprojection array 70, there are also a plurality of microprojections such as 76. The microprojection array comprises three layers 72, 74 and 78. However, in array 70 the layer 72 encompasses only a portion of the microprojections which comprises their tips or distal ends. Layer 72 may have a higher concentration of drug substance than layer 74. Layer 74 encompasses only a portion of the microprojections. Layer 78 encompasses the portion of the microprojections not contained in layers 72 or 74. It encompasses the totality of the base. In this type of microprojection array, the depth of drug substance delivered through the microprojection array can be controlled by tailoring the length of portion of tip 72.

In a further type of microprojection array 80 shown schematically in cross-section in FIG. 5B, there is also a plurality of microprojections such as 88. The microprojection array comprises a layer 82 which includes the distal ends of the microprojections. That layer, however, encloses deposits such as 84 which contain active. The layer 82 may be made of a material which serves to control the rate at which the active is released from the deposits 84. There are two further layers 86 and 90. Layer 86 may be made of a material eroding more rapidly than other layers, for example so as to allow separation of the microprojections 88 in use. Layer 90 encompasses the base of the array.

Example 8 discloses fabrication procedures by which microprojection arrays of the type of array 80 may be made. The materials for layer 82 need to be chosen so that the enclosure of the deposits 84 can be achieved. Exemplary polymers suitable for use in layer 82 include poly(lactic acid), poly(glycolic acid), poly(lactic acid-co-glycolic acid), poly(caprolactone), polyanhydrides, polyamines, polyesteramides, polyorthoesters, polydioxanones, polyacetals, polyketals, polycarbonates, polyphosphoesters, polyorthocarbonates, polyphosphazenes, poly(malic acid), poly (amino acids), hydroxycellulose, polyphosphoesters, polysaccharides, chitin, and copolymers, terpolymers and mixtures of these.

Figures 5C, 6:
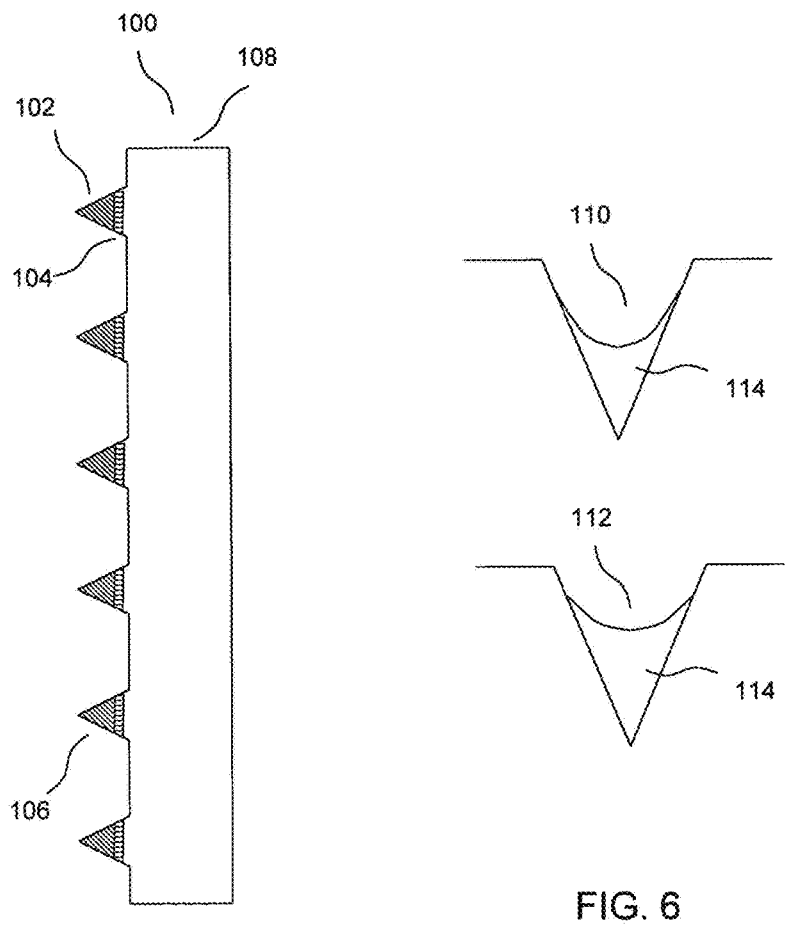
FIG. 6 depicts schematically possible shapes of the layer comprising the tips of microneedles after casting.

A further type of three-layer microprojection array 100 is shown schematically in cross-section in FIG. 5C. In array 100 there are also a plurality of microprojections such as 106. The microprojection array comprises three layers 102, 104 and 108. In array 100 the middle layer 104 may be made of a material eroding more rapidly than other layers, for example so as to allow separation of the microprojections 106 in use. In that event the drug substance is preferably contained in layer 102.

While FIGS. 5A-5C depict planar interfaces between the layers making up the microprojection arrays, in reality these interfaces may have a curvature. FIG. 6 depicts certain possible shapes 110 and 112 that the top of the lowermost layer 114 of an array may assume. Each of these shapes may be referred to generally as a "meniscus," although some people might strictly speaking limit that term to the shape of a liquid partially filling a cavity and not extend it to the shape of a cast composition in a cavity after solvent removal. It is known that the form of the meniscus of a liquid is affected by its density and by surface tension parameters, and may be modified by the use of surface-active agents. For the surface of a solvent-cast formulation in a cavity, it is further possible to affect the form of the surface by means of differential drying conditions, for example making it have greater or lesser curvature or to lie deeper or higher in the cavity. Example 10 provides some illustrations of drying regimes which can affect the form of the surface of the solvent-cast film following solvent removal.

In a method of the invention, the solution comprising the active is cast so that it fills the cavities of a mold partially or fills no more than the cavities. This solution is dried. A further solution with a lower or zero concentration of active, constituting a second layer, is then cast over the solution comprising the active. The polymers used in the first layer are preferably not soluble in the solvent used for the second layer. The second layer preferably uses a different polymer or polymers from the ones used in the first layer. This procedure may produce an array which array has two layers and in which the microprojections are enriched in active. In such an array, the active would not be expected to substantially diffuse into the first layer.

The second layer may comprise, for example, cellulose acetate butyrate, cellulose acetate, cellulose acetate propionate, ethyl cellulose, nitrocellulose, hydroxypropyl methyl cellulose phthalate, polystyrene, polyacrylates (such as acrylate/octylacrylamide copolymers, Dermacryl 97), polymethacrylates (such as Eudragits E, RL, RS, L100, S100, L100-55), or poly(hydroxyl alkanoates). Preferably the second layer may comprise biocompatible, biodegradable polymer(s) such as PLA, PGA, PLGA, polycaprolactone and copolymers thereof. Preferably where the first layer is cast in an aqueous solvent, the second layer is cast in an organic solvent. Preferred solvents for the second layer include alcohols, for example isopropyl alcohol and ethanol, and esters, for example ethyl acetate, heptane, or propyl acetate, or other solvents such as acetonitrile, dimethylsulfone (DMSO), N-methylpyrrolidone (NMP), or glycofurol.

In a multi-layer microprojection array, the first layer, instead of being placed into the mold by a method such as bulk casting, may alternatively be transported into each individual mold cavity as an individual droplet. In recent decades systems have been developed for putting down many small drops automatically onto substrates in a regular pattern. Such systems may operate, for example, on a piezoelectric or bubble jet principle. An early application of these capabilities was inkjet printing in which ink was impelled towards a substrate such as a sheet of paper according to a computer-controlled pattern. A variety of other types of liquids, including liquids containing biomolecules, have also been deposited by such techniques. Exemplary patents discussing this type of technology include U.S. Pat. Nos. 6,713,021, 6,521,187, 6,063,339, 5,807,522, and 5,505,777. Commercial products for such applications are available, for example, from BioDot, Inc. (Irvine, Calif.), MicroFab Technologies, Inc. (Plano, Tex.), and Literx Corporation (Pleasanton, Calif.).

A typical dispensing arrangement (see FIG. 3) uses a dispensing head 10 which is movable in an X-Y plane by means of a suitable apparatus 20. The dispensing head commonly comprises a reservoir of liquid, a pre-dispensing zone, and an opening into the pre-dispensing zone. The liquid in the pre-dispensing zone does not pass through the opening on account of surface tension. A transducer, typically piezoelectric, is operatively connected to the pre-dispensing zone. In operation, a pulsing of the transducer reduces the volume of the pre-dispensing zone and so imparts sufficient energy to the liquid in the pre-dispensing zone that surface tension is overcome and a drop is dispensed.

In addition to piezoelectric transducers, other ways of impelling the liquid from a dispensing head have been discussed in the literature. For example, a gas may be used, or the movement of a member driven by a magnetic field.

A major consideration favoring the placement of the first layer in the form of droplets into the mold cavity is the potential savings of drug substance that can result if the first layer is the only drug-containing layer. This can be of particular value if the drug substance is expensive.

A consideration in the placement of the first layer in the form of droplets is the variability in the size of the droplets which is placed in each cavity. It is preferred that the droplet volumes have a coefficient of variation of no more than about 25%, no more than about 15%, no more than about 10%, no more than about 5%, or no more than about 2%.

It is also desirable that the droplets arrive fairly precisely into the centers of the mold cavities so that following the process of filling they are located near the bottoms of the cavities. Cavity openings may typically have diameters on the order of approximately 100 μm. It may therefore be desired, for example, that the droplet center lie within a radius of about 15, 25, or 35 μm around the center of the cavity opening. As will be seen by the person of skill in the art, a number of factors go into determining whether this degree of precision can be achieved routinely. For example, the molds should have a dimensional stability which makes this degree of precision achievable. Their alignment relative to the dispensing device should also be controllable to the requisite degree of precision.

Figure 3:
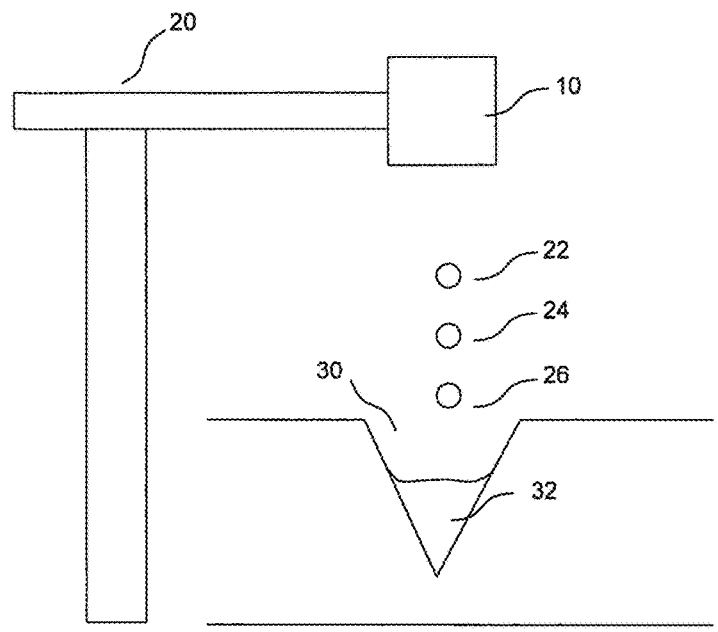
FIG. 3 depicts schematically a cavity in a mold being filled by means of droplets. The figure is not to scale and in particular the cavity and the droplets are shown with a very different scale from the dispensing head and the apparatus which moves the dispensing head.

Preferably the droplets would displace the air in the mold cavities so air would not be trapped inside the mold cavities under the formulation. Each droplet preferably enters the cavity into which it is transported without splashing or bouncing (i.e., remains in the cavity after being transported into it). In order to achieve this, it may be desirable to control the energy or velocity or momentum of the droplets at the time that they strike the cavity. Additional drops of formulation could be added to the cavities either before or after the formulation that was previously dispensed has dried. FIG. 3 depicts three droplets 22, 24, 26 in succession being transported into a cavity 30 which already contains liquid 32.

The diameter of the droplets is preferably smaller than the opening of the microneedle cavity in the mold. For example, a typical microneedle may be 200 μm long with a hexagonal base and a 10° draft on each face. The base of this microneedle would then be 71 μm from face to face. The volume of this microneedle is approximately 280 pL. The cavity in the mold to make this microneedle has approximately the same dimensions. A drop of fluid used to fill the cavity is preferably smaller in diameter than the opening of the cavity. To meet this constraint, the drop should consequently be less than 71 µm in diameter. A 71 µm diameter sphere has a volume of 187 pL. Thus, it may be desirable to dispense droplets in the range from about 50 pL to about 100 pL, about 150 pL, about 200 pL, about 250 pL, about 300 pL or about 500 pL, or about 1 nL.

The biodegradability of a microneedle array may be facilitated also by the inclusion of sugars. Exemplary sugars which may be included in a microneedle array include dextrose, fructose, galactose, maltose, maltulose, isomaltulose, mannose, lactose, lactulose, sucrose, and trehalose. Sugar alcohols, for example lactitol, maltitol, sorbitol, and mannitol, may also be employed. Cyclodextrins can also be used advantageously in microneedle arrays, for example α, β, and γ cyclodextrins, for example hydroxypropyl-β-cyclodextrin and methyl-β-cyclodextrin. Sugars and sugar alcohols may also be helpful in stabilization of certain actives (e.g., proteins) and in modifying the mechanical properties of the microprojections by a plasticizing-like effect.

The biodegradability of a microneedle array may be facilitated by inclusion of water-swellable polymers such as crosslinked PVP, sodium starch glycolate, celluloses, natural and synthetic gums, or alginates.

In a multilayer array, the sugars and other polymers which facilitate biodegradability may be located only in a layer or layers which encompass the microprojections.

The microneedle arrays of the invention are suitable for a wide variety of drug substances. Suitable active agents that may be administered include the broad classes of compounds such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof.

In general certain drug substances (e.g., nitroglycerin) will transport readily through skin, without any special formulation requirements. Other drug substances will transport through skin with greater difficulty and, with a practical-sized system for application, only with the assistance of enhancers. Other substances are not suitable for transdermal administration even with available enhancers and thus benefit particularly from the channels which microneedles are able to produce. Such substances include, for example, peptidic or other large molecule substances for which oral administration is also not an option.

Examples of peptides and proteins which may be used with microneedle arrays are oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumor necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gramicidines, growth hormones, melanocyte stimulating hormone, thyroid hormone releasing hormone, thyroid stimulating hormone, parathyroid hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof.

Macromolecular active agents suitable for microneedle array administration may also include biomolecules such as antibodies, DNA, RNA, antisense oligonucleotides, ribosomes and enzyme cofactors such as biotin, oligonucleotides, plasmids, and polysaccharides. Oligonucleotides include DNA and RNA, other naturally occurring oligonucleotides, unnatural oligonucleotides, and any combinations and/or fragments thereof. Therapeutic antibodies include Orthoclone OKT3 (muromonab CD3), ReoPro (abciximab), Rituxan (rituximab), Zenapax (daclizumab), Remicade (infliximab), Simulect (basiliximab), Synagis (palivizumab), Herceptin (trastuzumab), Mylotarg (gemtuzumab ozogamicin), CroFab, DigiFab, Campath (alemtuzumab), and Zevalin (ibritumomab tiuxetan).

Macromolecular active agents suitable for microneedle array administration may also include vaccines such as, for example, those approved in the United States for use against anthrax, diphtheria/tetanus/pertussis, hepatitis A, hepatitis B, *Haemophilus influenzae* type b, human papillomavirus, influenza, Japanese encephalitis, measles/mumps/rubella, meningococcal diseases (e.g., meningococcal polysaccharide vaccine and meningococcal conjugate vaccine), pneumococcal diseases (e.g., pneumococcal polysaccharide vaccine and meningococcal conjugate vaccine), polio, rabies, rotavirus, shingles, smallpox, tetanus/diphtheria, tetanus/diphtheria/pertussis, typhoid, varicella, and yellow fever.

In a further aspect of the invention, it may be desired that the microprojections of the array detach from the array following insertion of the array into skin.

One major advantage of detaching and dissolving microprojections is elimination of sharp disposal requirements.

Another advantage of detaching and dissolving microprojections is elimination of needle stick injury. Another advantage of detaching and dissolving microprojections is elimination of misuse, for example needle sharing, since the substrate without microprojections or with microprojections whose tips have been blunted due to biodegradation will not penetrate the skin. Another advantage of detaching and dissolving microprojections is the avoidance of drug misuse because drug enriched tips are dissolved in the skin and no or minimal drug is left in the array.

Detachable microprojections may be accomplished by a number of approaches. A layered approach, for example, may be used in which the array is composed of multiple layers, and a layer comprising the attachment areas of the microprojections to the array is more readily degradable than other layers. For example, the layer comprising the attachment areas of microprojections to array may be one which is more rapidly hydrated than the other layers.

Alternatively, an array made of a homogeneous material may be employed, in which the material is more readily degradable at lower pH's. Arrays made of such a material will tend to degrade more readily near the attachment points because these, being closer to the surface of the skin, are at a lower pH than the distal ends of the microprojections. (The pH of the skin's surface is generally lower than that of the skin further inwards, pH being for example approximately 4.5 on the surface and approximately 6.5 to 7.5 inward.)

Materials whose solubility is dependent on pH can be, for example, insoluble in pure water but dissolve in acidic or basic pH environment. Using such materials or combination of materials the arrays can be made to differentially biodegrade at skin surface (pH approximately 4.5) or inside skin. In the former, the whole array can biodegrade while in latter the microneedle portion of the array will biodegrade while substrate can be removed away.

Materials whose degradability in an aqueous medium is dependent on pH may be made, for example, by utilizing the acrylate copolymers sold by Rohm Pharma under the brand name Eudragit, which are widely used in pharmaceutical formulation. A further example of a material with pH variable solubility is hydroxypropyl cellulose phthalate.

Microneedle arrays made of materials with pH dependent solubility may have additional advantages besides facilitating detachment and differential absorption. For example, they may simplify packaging and handling because of their moisture resistance and rapid hydration and bioadhesion in the buffered acidic or basic environment of the skin.

Microprojection arrays may also be made in which the microprojections have a biodegradability which varies with temperature over the range of expected use conditions, for example in the range of about 25° C. to about 40° C. This may be achieved, for example, by the use of thermosensitive or thermoresponsive polymers. For example, PLGA biodegrades more slowly at higher temperatures. Certain Pluronic polymers are able to solidify with rising temperature. A use for the variation of degradability with temperature is, for example, due to the fact that the microprojections when inserted in skin will tend to have their distal ends at a higher temperature than the portions closer to the base, including the portions (if any) which are not inserted into skin and are thus at a temperature closer to the ambient temperature. The use of a temperature-dependent biodegradability thus offers a further way to tailor the biodegradability along the length of the microprojections.

In a further aspect of the invention, it may be desired that the microneedle array or a layer of the array comprise a polymer or polymer blend with certain bioadhesive characteristics, which within a certain range of moisture will have higher adhesive strength the greater the moisture. It is particularly preferred in a multilayer array that the layer or layers in which the microneedles principally lie possess bioadhesive characteristics.

While usable microneedles may be made of a number of biodegradable polymers as indicated in the patents and patent applications cited in the background section, a polymer that has a bioadhesive character has the advantage that no additional array attachment mechanism, for example an additional adhesive arranged along the exterior perimeter of the microneedle array, may be needed. Use of a bioadhesive polymer may also facilitate detachment of the microneedles or microprojections because they will have a greater adhesion to the interior of the skin where there is greater moisture.

The bioadhesive polymers used in the methods of the invention may, for example, increase in adhesiveness from a moisture content of about 2%, about 5%, or about 10% to some upper limit of moisture content. The upper limit of moisture content beyond which adhesiveness ceases to increase is preferably at least about 20%, more preferably at least about 30%, 40%, 50% or 60% moisture content.

Exemplary polymers with bioadhesive characteristics include suitably plasticized polyvinyl alcohol and polyvinylpyrrolidone. An extensive discussion of a class of bioadhesive polymer blends is found in U.S. Pat. No. 6,576,712 and U.S. Published Patent Applications Nos. 2003/0170308 and 2005/0215727, which are incorporated by reference for their teaching of bioadhesive polymer blends and adhesion testing. Preferable bioadhesive polymers are those which possess hydrogen-bonded crosslinks between strands of the primary polymers. These crosslinks may comprise a comparatively small molecule which forms hydrogen bonds to two primary polymer strands. It is believed that certain sugars may act as a small molecule crosslinker in this manner with particular primary polymers such as polyvinyl alcohol.

The bioadhesive character of a polymer or blend may be determined by testing the bulk material for adhesion (e.g., by a peel test) at different levels of hydration. Alternatively, the bioadhesive character may also be seen if a microneedle array as applied to skin becomes more difficult to remove in minutes or tens of minutes after application, since the array may be assumed to become more hydrated during that period of time.

The bioadhesive nature of polymer may allow the polymer to form a channel or plug in the skin to keep pores open for prolonged period of time for drug diffusion. This is particularly useful if the substrate of the array is used as a drug reservoir, containing the same active ingredient or a different active ingredient from the one contained in the microneedles. The bioadhesive array can be also be used to pretreat the skin and leave bioadhesive microneedles inside the skin. This may be followed by application of a solid or liquid reservoir. Due to the channel formation, drug may freely diffuse through bioadhesive channels created and located in the skin.

A bioadhesive array embedded in skin or in another membrane may also be used as a biosensor. It may respond, for example, to biomarkers, pH, hydration, or temperature by itself. Alternatively, it may facilitate the flow of matter from inside the skin through the bioadhesive channel and onto the base or a reservoir placed in the skin adjacent to the array. For example, if the rate of dissolution of microprojections in skin is correlated with some property of the skin (e.g., pH), that property may be measured by embedding microprojections in skin for a measured period of time and then observing the degree to which they have dissolved.

Because microprojection arrays penetrate human skin, it may be desirable to take steps which tend to eliminate the presence of microorganisms in the array. Such steps include, for example, the use of a formulation with high sugar concentration which will act as an osmotic agent to dehydrate microorganisms in the formulation. An alternative technique is the use of a non-physiological pH (e.g., below pH 6 and above pH 8) to retard growth and destroy microbial viability. The formulation may be made with organic solvents which are then dried in order to dehydrate microorganisms. Apart from the dehydration effect, the use of organic solvents is also inherently bactericidal since they disrupt bacterial cell membranes. In addition, the microprojection arrays may be packaged in a sealed, low oxygen environment to retard aerobic microorganisms and eventually destroy their viability. The arrays may also be packaged in a low moisture environment to dehydrate microorganisms.

A further technique to deal with microorganisms is to include a pharmaceutically acceptable antibacterial agent in the formulation or the packaging. Examples of such agents are benzalkonium chloride, benzyl alcohol, chlorbutanol, meta cresol, esters of hydroxyl benzoic acid, phenol, and thimerosal.

As a further alternative, a surfactant or detergent can be added to the formulation to disrupt the cell membrane of any microorganisms to kill them. A desiccant could be added to the packaging to dehydrate microorganisms and kill them.

Antioxidants may be added to the formulation, for example to protect the active from oxidation. Exemplary antioxidants include methionine, cysteine, D-alpha tocopherol acetate, DL-alpha tocopherol, ascorbyl palmitate, ascorbic acid, butylated hydroxyanisole, butylated hydroxyquinone, butylhydroxyanisole, hydroxycomarin, butylated hydroxytoluene, cephalin, ethyl gallate, propyl gallate, octyl gallate, lauryl gallate, propylhydroxybenzoate, trihydroxybutyrophenone, dimethylphenol, ditertbutylphenol, vitamin E, lecithin, and ethanolamine.

In the evaluation of solvent cast or other microneedle arrays, various figures of merit may be employed. A simple visual figure of merit is the completeness of the array under microscopic examination: are any of the microneedles of an unsuitable shape, for example broken off or with unduly blunt or fine ends? It is desirable that no more than about 20%, no more than about 10%, preferably no more than about 5%, and more preferably no more than about 2% of the microneedles have an unsuitable shape upon demolding.

An alternative figure of merit may be obtained by setting up a consistent test for skin penetration efficiency. An exemplary test requires the placement of the microneedle array upon a test sample of cadaver skin, the insertion of the array with a reproducible or standardized force, and the withdrawal of the array after a period of time. At that time the percentage of openings in the skin sample that are deemed to allow adequate transport of material may be taken as a figure of merit. A material that may be used to test adequacy of transport is India ink. It is desirable that at least about 80%, preferably at least about 90%, and more preferably at least about 95% of the openings in the skin allow adequate transport of material.

A further figure of merit for microneedle arrays is transepidermal water loss (TEWL) after application of the array, which is conveniently expressed in units of mass per unit area and time. TEWL measurement has a number of dermatological applications. Commercially available instruments exist for the measurement of TEWL, for example from Delfin Technologies Ltd., Kuopio, Finland. TEWL is conveniently measured before and after the application of a microneedle array to a human test subject, the ratio of the two measured values being an indication of the degree to which the microneedle array disrupts the barrier function of the skin.

For microneedle arrays it may be desired that the ratio of TEWL's after and before application of the microneedles be at least about 1.5, at least about 2.0, more preferably at least about 2.5.

In practice, it may often be helpful for the microneedles produced by processes of the invention to be applied to the skin by means of some mechanism which helps insure a greater uniformity in the skin penetration efficiency. Such mechanisms may include, for example, the applicators disclosed in U.S. Provisional Patent Application No. 60/881,905, which is incorporated by reference.

It is to be understood that while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

The following examples are put forth so as to provide those of ordinary skill in the art with a complete disclosure and description of how to implement the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE 1

General Process for Array Casting

The mold to be used to form a microneedle array is cleaned with water or other suitable solvent and dried in an incubator. The mold is then placed in a Petri dish. One dispenses a small amount of formulation, for example, 20 µL, on the mold. The formulation may contain, for example, 25% bovine serum albumin (BSA), 20% polyvinyl alcohol, 27% trehalose, and 28% maltitol in water solvent, such that the formulation has, for example, 20% solids content as applied. The formulation is spread manually over the mold using a transfer pipette with a trimmed tip. The formulation is then vortexed, for example for five seconds, using a commercial vibrating instrument to even out the formulation. The mold with the formulation covering it is placed in a pressure vessel under 1 atm for about 10 minutes. Pressure is then removed. The mold is placed in an incubator at a temperature of 32° C., for about 1 hr. The array may then be demolded, for example using double-sided adhesive tape, and optionally attached to a backing.

EXAMPLE 2

General Process for Casting Two-Layer Arrays

Following the drying step of Example 1, an additional layer is cast on the mold using similar procedures. The additional layer may, for example, consist of 75 μL of 20 wt % Eudragit EPO in a 3:1 mixture of ethanol and isopropyl alcohol. The additional layer may be spread out, for example, using a glass slide. The mold is placed in a pressure vessel and pressurized at 1 atm for 2 minutes. The pressure is released and the mold is allowed to dry in the pressure vessel for an additional five minutes, without disturbing. The mold is again dried in the incubator for 1 hr at 32° C., and then demolded.

EXAMPLE 3

Solvent-Cast Microneedle Arrays Comprising Polyvinyl Alcohol

Microneedle arrays were cast from polyvinyl alcohol (PVA) using bovine serum albumin (BSA) as a model drug, water as a solvent, and proportions of PVA, BSA, and other ingredients as indicated below. The general procedure of Example 1 was followed with some variations. Each array was evaluated by microscopic examination. The details of the arrays and their evaluations are given in the table below.

| Ex. # | BSA % | PVA USP, % | Trehalose % | Other ingredients | Solids in casting solution % | BSA in casting solution % | Evaluation |
|---|---|---|---|---|---|---|---|
| A1 | 0 | 100 | | | 10 | 0 | clear, good |
| A2 | 25 | 75 | | | 8.0 | 2.0 | good |
| A3 | 25 | | | 75% 22 kD PVA | 13.3 | 3.3 | good |
| A4 | 25 | 25 | | 50% mannitol | 15.8 | 3.9 | white, good |
| A5 | 25 | 25 | | 50% HP-β-CD | 15.8 | 3.9 | clear, good |
| A6 | 25 | 25 | 50 | | 16.1 | 3.9 | clear good |
| A7 | 5 | 25 | | 70% mannitol | 22.0 | 1.1 | white, OK |
| A8 | 5 | 32.2 | | 62.8% mannitol | 15.4 | 0.8 | white, OK |
| A9 | 5 | 32.2 | 62.8 | | 15.4 | 0.8 | clear, good |
| A10 | 5.4 | 29.9 | 44.8 | 19.9% HP-β-CD | 15.9 | 0.9 | clear, good |
| A11 | 5 | 24.8 | 49.6 | 20.7% HP-β-CD | 18.4 | 0.9 | clear, good |
| A12 | 5 | 24.8 | 49.5 | 20.7% PVP K30 | 20.6 | 1 | clear, good |
| A13 | 5 | 20 | 50 | 25% HP-β-CD | 20.3 | 1 | clear, good |
| A14 | 5 | 20 | 30 | 15% HP-β-CD, 30% maltitol | 20.3 | 1 | clear good |
| A15 | 5 | 20 | 25 | 10% HP-β-CD, 40% mannitol | 20.3 | 1.0 | white, good |
| A16 | 5.1 | | 25.6 | 9.9% HP-β-CD, 39.6% mannitol | 28.9 | 1.5 | white, good |
| A17 | 5 | 20.1 | 34.9 | 30% mannitol, 10% Lutrol 68 | 21.8 | 1.1 | white, goad |
| A18 | 21 | — | — | 52% 22K PVA 26% sucrose | 22.8 | 4.8 | white, good |

In this table, percentages are by weight, the mannitol is always D-mannitol, and HP-β-CD means hydroxypropyl β-cyclodextrin.

The following table gives the evaluation of a further set of microneedle arrays.

| Ex. # | BSA % | PVA USP, % | Tre-halone % | Other ingredients | Solids in casting solution % | BSA in casting solution % | Evaluation |
|---|---|---|---|---|---|---|---|
| A19 | 40 | 20 | 20 | 20% maltitol | 15.6 | 6.3 | clear, good |
| A20 | 30 | 20 | 25 | 25% maltitol | 18.2 | 5.5 | clear, good |
| A21 | 25 | 20 | 27 | 28% maltitol | 16.3 | 4.07 | clear, good |

It is seen from the tables above that a wide variety of compositions can result in acceptable microneedle arrays.

EXAMPLE 4

Casting Two-Layer Arrays

A microneedle array with two layers can be prepared by the following steps:

1) Casting a solution comprising an active, polymer, and possibly other components in a mold. The clean mold is placed in a mold holder. One dispenses a small amount of formulation, for example, 75 μL, as a droplet on the mold, placing a cover slip on top of the droplet to help spread the liquid onto the whole surface of the mold. The formulation may contain, for example, 15% human parathyroid hormone 1-34 fragment (hPTH1-34), 65% dextran 70, 20% sorbitol in a histidine buffer solvent, such that the formulation has, for example, 30% solids content as applied. The mold with the formulation covering it is placed in a pressure vessel under ca. 50 psi for about 30 seconds. Pressure is then removed. The excess formulation is wiped with a silicone wiper with the interference between wiper edge and surface of mold about 1-10 mils. The mold is placed in an incubator at a temperature of 32° C., for about half an hour.

2) Casting an additional layer on top of the first layer in the mold. The mold with drug-containing layer cast is removed from the drying oven, any residue of dry formulation left on the base of the mold is removed by tape strip using a 3M 1516 single-sided adhesive. Then about 150 μL of "basement" solution which comprises poly(lactic acid-co-glycolic acid) (PLGA) with L/G ratio of 75/25 in acetonitrile is placed on the mold (atop the first solution). A thin film is cast using a wiper with the clearance between edge of the wipe and the surface of the mold about 10-20 mil. The mold is then placed into a pressure vessel under 10-30 psi with controlled venting for about 5 min. The mold is further dried at room temperature for about 30 min. The array may then be demolded, for example using double-sided adhesive tape, and optionally attached to a polyethylene terephthalate film as backing.

EXAMPLE 5

Solvent-Cast Microneedle Arrays Comprising Polyvinyl Alcohol, Dextran, Tetrastarch and Other Excipients Microneedle arrays were cast from PVA with sucrose as a sugar excipient, or dextran with sorbitol as a sugar excipient, or tetrastarch with sorbitol as a sugar excipient, bovine serum albumin (BSA) as a model drug, and histidine buffer, pH 5-6, as a solvent. The proportions of polymer, sugar and drug are indicated below. The general procedure of Example 4 was followed with some variations. The details of the formulations used to form the arrays are given in the table below.

| Ex. # | Polymer | | Sugar | | BSA | Solids in Casting solution |
|---|---|---|---|---|---|---|
| | Type | Wt % | Type | Wt % | Wt % | Wt % |
| B1 | PVA | 54.5 | Sucrose | 27.2 | 18.2 | 22 |
| B2 | PVA | 54.5 | Sucrose | 18.2 | 27.2 | 22 |
| B3 | Dextran 70 | 71 | Sorbitol | 14 | 14 | 28 |
| B4 | Dextran 70 | 67 | Sorbitol | 20 | 13 | 30 |
| B5 | Dextran 40 | 75 | Sorbitol | 12 | 13 | 28 |
| B6 | Dextran 40 | 65 | Sorbitol | 23 | 12 | 30 |
| B7 | Tetrastarch | 67 | Sorbitol | 20 | 13 | 30 |
| B8 | Tetrastarch | 75 | Sorbitol | 13 | 12 | 25 |

The following table gives the details of formulations to form microneedle arrays with hPTH(1-34) as the drug substance.

| Ex. # | Polymer | | Sugar | | hPTH (1-34) | Solids in casting solution |
|---|---|---|---|---|---|---|
| | Type | Wt % | Type | Wt % | Wt % | Wt % |
| B9 | PVA | 52.6 | Sucrose | 26.3 | 21.1 | 22.8 |
| B10 | PVA | 46.2 | Sucrose | 23.1 | 30.7 | 26 |
| B11 | Dextran 70 | 67.5 | Sorbitol | 14 | 18.5 | 33 |
| B12 | Dextran 70 | 64.9 | Sorbitol | 19.5 | 15.6 | 30.8 |
| B13 | Dextran 40 | 67.5 | Sorbitol | 14 | 18.5 | 33 |
| B14 | Dextran 40 | 64.9 | Sorbitol | 19.5 | 15.6 | 30.8 |
| B15 | Tetrastarch | 67.5 | Sorbitol | 14 | 18.5 | 33 |
| B16 | Tetrastarch | 64.9 | Sorbitol | 19.5 | 15.6 | 30.8 |
| B17* | Dextran 70 | 64.8 | Sorbitol | 19.3 | 15.5 | 31.2 |

*ca. 0.4 wt % of methionine is added to the formulation as an antioxidant agent.

It is seen from the tables above that a wide variety of compositions can be used to form microneedle arrays in accordance with this invention.

EXAMPLE 6

Polymeric Solutions for Casting "Basement" Layers of Microneedle Arrays

Different polymeric solutions can be used for casting the basement layer for the microneedle arrays. The polymer solutions are prepared by dissolving the polymers in a solvent or solvent mixture at room temperature with polymer concentration about 15-30% by weight. The details of composition of certain polymer solutions used for casting the basement of microneedle arrays are summarized in the table below.

| Ex. # | Polymer | | Solvent | |
|---|---|---|---|---|
| | Type | Wt % | Type | Wt % |
| C1 | Eudragit EPO 100 | 20 | Ethanol/IPA 3/1 | 80 |
| C2 | Eudragit EPO 100 | 30 | Ethanol/IPA 3/1 | 70 |
| C3 | Eudragit EPO 100/PVP (1:1) | 20 | Ethanol/IPA 3/1 | 80 |
| C4 | PLGA (75/25) | 10 | Ethyl acetate | 90 |
| C5 | PLGA (75/25) | 15 | Ethyl acetate | 85 |
| C6 | PLGA (75/25) | 15 | Acetonitrile | 85 |
| C7 | PLGA (75/25) | 20 | Acetonitrile | 80 |
| C8 | PLGA (75/25) | 30 | Acetonitrile | 70 |
| C9 | PLGA (65/35) | 20 | Acetonitrile | 80 |
| C10 | PLA | 20 | Acetonitrile | 80 |
| C11 | Polycaprolactone | 20 | Acetonitrile | 80 |

In this table the following abbreviations are used: Polyvinylpyrrolidone (PVP); poly(lactic acid-co-glycolic acid) (PLGA) (L/G ratio 75/25, 65/35); poly(lactic acid) (PLA); and isopropyl alcohol (IPA).

EXAMPLE 7

Casting Microneedle Arrays with Three Layers

A microneedle array with three layers can be prepared in the following steps:
1) Casting a non-drug containing tip layer in the mold. The clean mold is placed in a mold holder. One dispenses a small amount (20 μL) of formulation solution without drug, as a droplet on the mold. The formulation may contain, for example, 70% dextran 70, 30% sorbitol in histidine buffer solvent, such that the formulation has, for example, 30% solids content as applied. The mold with the formulation covering it is placed in a pressure vessel under ca. 50 psi for about 30 seconds. Pressure is then removed. The excess formulation is wiped with a silicone wiper with the interference between wiper edge and surface of mold about 1-10 mils. The mold is placed in an incubator at a temperature of 32° C., for about half an hour.

2) Casting drug containing layer in the mold. After the step 1) above, one dispenses a small amount of formulation, for example, 75 µL, as a droplet on the mold, place a cover slip on top of the droplet to help spread the liquid onto the whole surface of the mold. The formulation may contain, for example, 15% human parathyroid hormone 1-34 fragment (hPTH(1-34)), 65% dextran 70, 20% sorbitol in histidine buffer solvent, such that the formulation has, for example, 30% solids content as applied (e.g., B12 in Example 5 above). The mold with the formulation covering it is placed in a pressure vessel under ca. 50 psi for about 30 seconds. Pressure is then removed. The excess formulation is wiped with a silicone wiper with the interference between wiper edge and surface of mold about 1-10 mils. The mold is placed in an incubator at a temperature of 32° C., for about half an hour.

3) Casting the basement layer on top of the drug-containing layer in the mold. After step 2) above, then about 150 µL of basement solution which comprises poly(lactic acid-co-glycolic acid) (PLGA) with L/G ratio of 75/25 in acetonitrile is placed on the mold (on top of the drug-containing layer). A thin film is cast using a wiper with the clearance between edge of the wipe and surface of the mold about 10-20 mil. The mold is then placed into a pressure vessel under 10-30 psi with controlled venting for about 5 min. The mold is further dried at room temperature for about 30 min. The array may then be demolded, for example using double-sided adhesive tape, and optionally attached to a polyethylene terephthalate film as backing.

EXAMPLE 8

Casting Arrays with a Rate Controlling Layer

A microneedle array with a rate controlling layer can be prepared in the following steps:

1) Casting a thin film of PLGA at the bottom of each cavity of the mold. The clean mold is placed in a mold holder. One dispenses a small amount (for example 20 µL) of PLGA solution (for example solution C4 of Example 4) as a droplet on the mold. A thin film is cast using a wiper, with the clearance between the edge of the wiper and the surface of the mold being about 1-5 mils. The mold is then placed into a pressure vessel under 10-30 psi for about 30 sec. Pressure is then removed. The excess formulation is wiped with a silicone wiper, with the interference between wiper edge and the mold surface about 1-10 mils. The mold is placed in an incubator at a temperature of 32° C., for about half an hour. Additional steps may be taken to ensure that the thin film of PLGA is spread over the sides of the mold cavity.

2) Casting a drug-containing solution. After the step 1) above, one dispenses a small amount of formulation, for example, 75 µL, as a droplet on the mold, placing a cover slip on top of the droplet to help spread the liquid onto the whole surface of the mold. The formulation may contain, for example, 15% human parathyroid hormone 1-34 fragment (hPTH(1-34)), 65% Dextran 70, 20% sorbitol in histidine buffer solvent, such that the formulation has, for example, 30% solids content as applied (e.g., B 12 in Example 5 above). The mold with the formulation covering it is placed in a pressure vessel under ca. 50 psi for about 30 seconds. Pressure is then removed. The excess formulation is wiped with a silicone wiper with the interference between wiper edge and surface of mold about 1-10 mils. The mold is placed in an incubator at a temperature of 32° C., for about half an hour.

3) Casting a thin layer of PLGA on top of the drug-containing layer in the mold. The mold with drug-containing layer cast is removed from the drying oven. Any residues of dry formulation left on the base of the mold are removed by tape strip using a 3M 1516 single-sided adhesive. One then places on the mold, on top of the drug-containing layer, about 10 µL of polymer solution which comprises poly (lactic acid-co-glycolic acid) (PLGA) with L/G ratio of 75/25 in acetonitrile. A thin film is cast using a wiper with the clearance between edge of the wipe and surface of mold about 1-5 mil. The mold is then placed into a pressure vessel under 10-30 psi with controlled venting for about 30 seconds. The mold is further dried at room temperature for about 30 min.

4) Casting a dissolvable layer on top of the thin PLGA layer. After step 3) above, one dispenses a small amount of formulation, for example, 25 µLL as a droplet on the mold and places a cover slip on top of the droplet to help spread the liquid onto the whole surface of the mold. The formulation may contain, for example, 70% Dextran 70, 30% sorbitol in histidine buffer solvent, such that the formulation has, for example, 30% solids content as applied. The mold with the formulation covering it is placed in a pressure vessel under ca. 50 psi for about 30 seconds. Pressure is then removed. The excess formulation is wiped with a silicone wiper with the interference between wiper edge and surface of mold about 1-8 mils. The mold is placed in an incubator at a temperature of 32° C., for about half an hour.

5) Casting a basement layer on top of the dissolvable layer in the mold. After step 4) above, then about 150 µL of basement solution which comprises poly(lactic acid-co-glycolic acid) (PLGA) with L/G ratio of 75/25 in acetonitrile is placed on the mold (on top of the drug-containing solution). A thin film is cast using a wiper, with the clearance between edge of the wipe and surface of mold about 10-20 mil. The mold is then placed into a pressure vessel under 10-30 psi with controlled venting for about 5 min. It is believed that this pressure treatment helps to tailor the depth where the active pharmaceutical ingredient (drug substance) is delivered. The mold is further dried at room temperature for about 30 min. The array may then be demolded, for example using double-sided adhesive tape, and optionally attached to a polyethylene terephthalate film as backing.

EXAMPLE 9

Casting Arrays for Sustained Release of Drug Substance from the Array

A microneedle array for sustained release of drug substance from the array can be prepared in the following steps:

1) Casting a drug-containing layer for sustained release of drug substance. The clean mold is placed in a mold holder. One dispenses a small amount (e.g., 75 µL) of aqueous solution which comprises hPTH(1-34), a polymeric matrix such as polyethylene glycol-co-poly(lactic acid-co-glycolic acid) (PEG-PLGA) copolymer, and excipients such as sucrose or sorbitol. The polymeric matrix is generally amphiphilic in nature. The hydrophobic segment(s) of the polymer can help control the release of drug substance.

Examples of such formulations are described in the table below. The liquid formulation is spread manually on the surface of the mold with a glass cover slip. The mold with the formulation covering it is placed in a pressure vessel under ca. 50 psi for about 30 seconds. Pressure is then removed. The excess formulation is wiped with a silicone wiper with the interference between wiper edge and surface of mold about 1-10 mils. The mold is placed in an incubator at room temperature for about half an hour.

The following table gives the details of aqueous solutions to form microneedle arrays, comprising drug substance hPTH, polymeric matrix and excipients.

| Ex. # | Polymer Type | Wt % | Excipients Type | Wt % | hPTH (1-34) Wt % | Solids in casting solution Wt % |
|---|---|---|---|---|---|---|
| D1 | PEG-PLGA (50/50(65/35)) | 50 | Sucrose | 35 | 15 | 10 |
| D2 | PEG-PLGA (50/50(65/35)) | 45 | Sucrose | 40 | 15 | 10 |
| D3 | PEG-PLGA (50/50(65/35)) | 45 | Sucrose | 40 | 15 | 20 |
| D4 | PEG-PLGA (50/30(65/35)) | 55 | Sucrose | 35 | 10 | 10 |
| D5 | PEG-PLGA (50/30(65/35)) | 55 | Sucrose | 35 | 10 | 10 |
| D6 | PEG-PLGA (50/30(65/35)) | 55 | Sorbitol | 35 | 10 | 10 |
| D7 | PEG-PLGA (50/50(65/35)) | 45 | Sorbitol | 40 | 15 | 10 |
| D8 | Pluronic F68 | 50 | Sucrose | 35 | 15 | 25 |
| D9 | Pluronic F127 | 50 | Sucrose | 35 | 15 | 15 |
| D10 | Pluronic F68 | 50 | Sorbitol | 35 | 15 | 25 |
| D11 | Pluronic F127 | 50 | Sorbitol | 35 | 15 | 15 |

In the table above, PEG-PLGA denotes a blend of polyethylene glycol and poly(lactic acid-co-glycolic acid).

2) Casting a dissolvable layer on top of the drug-containing layer in the mold. After the step 1) above, one dispenses a small amount of formulation, for example, 25 µL, as a droplet on the mold, place a cover slip on top of the droplet to help spread the liquid onto the whole surface of the mold. The formulation may contain, for example, 70% Dextran 70, 30% sorbitol in histidine buffer solvent, such that the formulation has, for example, 30% solids content as applied. The mold with the formulation covering it is placed in a pressure vessel under ca. 50 psi for about 30 seconds. Pressure is then removed. The excess formulation is wiped with a silicone wiper with the interference between wiper edge and the surface of the mold about 1-8 mils. The mold is placed in an incubator at a temperature of 32° C., for about half an hour.

3) Casting a basement layer on top of the dissolvable layer in the mold. After step 2) above, then about 150 µL of basement solution which comprises poly(lactic acid-co-glycolic acid) (PLGA) with L/G ratio of 75/25 in acetonitrile is placed on the mold (on top of the dissolvable layer) and thin film is cast using a wiper with the clearance between edge of the wipe and surface of mold about 10-20 mil. The mold is then placed into a pressure vessel under 10-30 psi with controlled venting for about 5 min. The mold is further dried at room temperature for about 30 min. The array may then be demolded, for example using double-sided adhesive tape, and optionally attached to a polyethylene terephthalate film as backing.

EXAMPLE 10

Casting Arrays with a Controlled Meniscus

The meniscus of the drug-containing layer in a solvent cast microneedle array manufacturing process might need to be controlled, for example to improve the consistency of skin penetration or improve efficiency. The meniscus can be controlled during the casting process as described below during the drying process:

The clean mold is placed in a mold holder. One dispenses a small amount (20 µL) of formulation solution without drug, as a droplet on the mold. The formulation may contain, for example, 70% Dextran 70, 30% sorbitol in histidine buffer solvent, such that the formulation has, for example, 30% solids content as applied. The mold with the formulation covering it is placed in a pressure vessel under ca. 50 psi for about 30 seconds. Pressure is then removed. The excess formulation is wiped with a silicone wiper with the interference between wiper edge and surface of mold about 1-10 mils.

One instance of controlling the meniscus of the drug-containing layer is to manage the initial drying of the drug-containing layer as follows: place the mold back in the pressure vessel under ca. 30 psi with controlled venting for 5-10 min, as an initial drying. Pressure is then removed. The mold is further dried in the incubator at a temperature of 32° C., for about 20-30 min.

Another instance of controlling the meniscus of the drug-containing layer is to manage the initial drying of the drug-containing layer as follows: the mold is placed back in a controlled humidity chamber with 50-75% RH for 5-10 min, as an initial drying. Pressure is then removed. The mold is further dried in the incubator at a temperature of 32° C., for about 20-30 min.

EXAMPLE 11

Skin Penetration Efficiency of Arrays with .About.50% Sugar Content

Two sets of arrays, E1 and E2, were prepared as described above. Arrays of type E1 were cast from a water solution of 25% by weight bovine serum albumin (BSA), 25% polyvinyl alcohol USP, and 50% trehalose. The water solution contained approximately 16.1% solids content. Arrays of type E2 were (i) cast from a water solution containing approximately 16.3% solids content, which consisted of 25% BSA, 20% polyvinyl alcohol USP, 27% trehalose, and 28% maltitol, producing a layer comprising the microneedles and a portion of the base, and then (ii) cast from 20 wt % Eudragit EPO in 3:1 ethanol:isopropyl alcohol, producing a second layer comprising a portion of the base. Both types of arrays had 200 µm high microneedles with a 400 µm spacing between microneedles. The arrays were 10 mm in diameter. Three arrays of each type were tested.

Skin penetration efficiency was tested using cadaver skin. The donor was a 77 year old white female. The skin was mounted on a foam-cork base and blotted on the stratum corneum side to remove excess moisture and to check for holes.

The microneedle arrays were placed needle-side down directly on skin, the arrays being in contact with skin for less than fifteen seconds. A portable spring-loaded impactor with a 10 mm tip was used to drive the microneedles into skin by impact loading. The impactor was used to hold arrays in skin for one minute. The arrays were then pulled out of the skin. A certain effort was required to pry the arrays out of the skin, confirming that the arrays possessed bioadhesive properties. India ink was used to stain the sites to confirm penetration.

Figure 1:
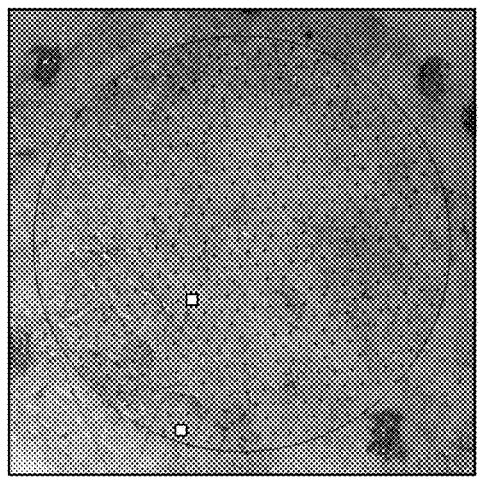
FIG. 1 is an exemplary chart of skin penetration efficiency from the arrays described in Example 11.
Figure 2:
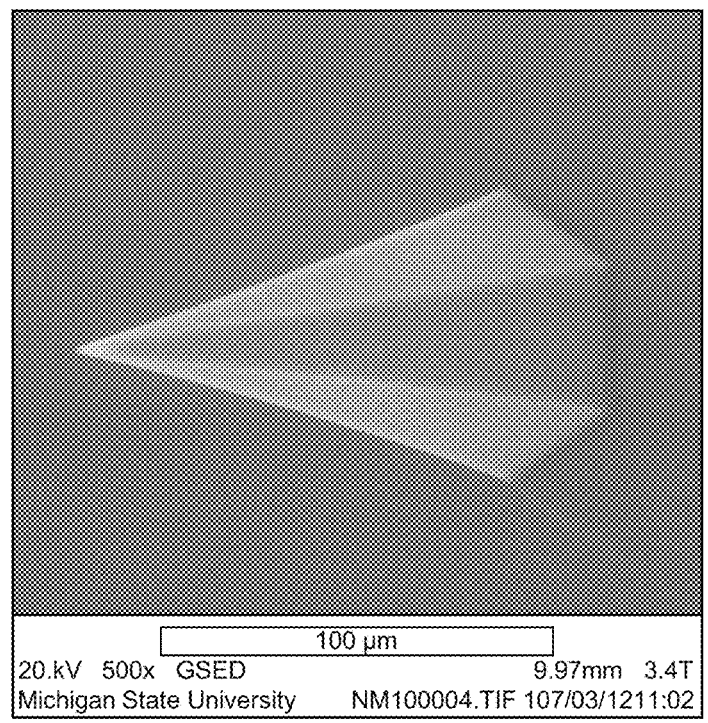
FIG. 2 is a scanning electron micrograph of a microneedle produced by processes of the invention.

FIG. 1 depicts the skin penetration efficiency measurement for a E2 array. Small squares (two in the figure) are used to mark places where penetration was deemed insufficient. Skin penetration efficiency was rated at 99.6%. Skin penetration efficiency is estimated by counting the number of relatively dark stained areas (holes) in the microneedle-treated skin region relative to the number of microneedles on the array used to treat the skin.

EXAMPLE 12

TEWL, SPE and Dissolution Tests of Arrays

The following data pertain to microneedle arrays of type E3, cast from a water solution (approximately 20.3% solids content) comprising BSA 5 wt %, PVA USP 20 wt %, hydroxypropyl β-cyclodextrin 15 wt %, trehalose 30 wt %, and maltitol 30 wt %. Data are also given for arrays of type E2 from Example 11 and for polysulfone (PSF) arrays, which do not dissolve.

| Array Type | Application Time | Pre TEWL | Post TEWL | TEWL Ratio | SPE | Needle Dissolution % Array | % Length |
|---|---|---|---|---|---|---|---|
| E3 | 2 min | 10.9 | 16.9 | 1.6 | >90% | 100% | 80% |
| E3 | 2 min | 5.8 | 16.9 | 2.9 | >90% | 90% | 80% |
| E3 | 2 min | 4.6 | 18.3 | 4.0 | >90% | 90% | 80% |
| E3 | 2 min | 3.7 | 22.9 | 6.2 | >90% | 90% | 80% |
| E3 | 2 min | 8.5 | 20.4 | 2.4 | >90% | 90% | 70% |
| E2 | 2 min | 8.9 | 26.9 | 3.0 | >90% | 90% | 80% |
| E2 | 2 min | 6.4 | 25.2 | 3.9 | >90% | 90% | 80% |
| E2 | 2 min | 5.5 | 23.1 | 4.2 | >90% | 90% | 80% |
| E2 | 2 min | 4.7 | 17.2 | 3.7 | >90% | 90% | 60% |
| E2 | 2 min | 7.4 | 18.3 | 2.5 | >90% | 90% | 70% |
| PSF | 2 min | 6.0 | 26.8 | 4.5 | >90% | NA | NA |
| PSF | 2 min | 6.3 | 18.5 | 3.0 | >90% | NA | NA |
| PSF | 2 min | 4.9 | 15.1 | 3.1 | >90% | NA | NA |

In this table the TEWL data were obtained using anesthetized laboratory rats. The SPE (skin penetration efficiency) is measured by using India ink. The % Array needle dissolution value indicates the percentage of microneedles in the array that showed some dissolution, whereas the % Length indicates the percentage of the total length of the microneedles which dissolved. The dissolution was estimated by observing the needles under the microscope after use.

EXAMPLE 13

Surface Treatment to Improve Wetting

Sylgard 184 silicone elastomer from Dow Corning (Midland, Mich.) was given a surface treatment to improve wetting as follows. A quartz glass ring surrounded by a polyurethane ring were placed atop a 5 mm thick sheet of Sylgard 184. These formed a basin in which a monomer solution was placed. Methacrylic acid 1.58 g, water 14.42 g, benzyl alcohol 0.14 g, and NaIO$_4$ 0.0022 g were placed in the basin. A total dose of 9.98 J/cm$^2$ of ultraviolet radiation was applied using an H type ultraviolet bulb three inches above the substrate. A conveyor was used to move the substrate past the ultraviolet bulb at 4 feet/minute for four passes. A UV Fusion Systems Model P300M was used for the ultraviolet exposure.

Wetting was measured by placing 10 µL drops of particular liquids on the treated and untreated silicone elastomer. The results are given in the following table (standard deviations in parentheses, N=3):

| Liquid | Drop Size on Untreated Surface (mm$^2$) | Drop Size on Treated Surface (mm$^2$) |
|---|---|---|
| n-propanol | 27.8 (2.2) | 30.5 (2.4) |
| 50% n-propanol | 18.8 (1.7) | 25.8 (1.2) |
| water | 9.3 (0.5) | 13.2 (2.1) |

A similar experiment was carried out in which the Sylgard 184 was pretreated with a 1% solution of benzophenone in heptane and dried for 15 minutes at 32° C. A solution containing acrylic acid 5 g, benzyl alcohol 0.35 g, NaIO$_4$ 0.035 g, and water 45 g was applied to pretreated Sylgard 184. In both cases doses of approximately 9.6 J/cm$^2$ of ultraviolet light were applied in a similar manner to the preceding experiment. The results are given in the following table:

| Liquid | Drop Size with Methacrylic Acid Solution (mm$^2$) | Drop Size With Acrylic Acid Solution (mm$^2$) |
|---|---|---|
| n-propanol | 52.2 (2.0) | 56.7 (8.7) |
| 50% n-propanol | 250.0 (20.0) | 150.0 (10.5) |
| water | 37.5 (4.0) | 31.7 (6.3) |

EXAMPLE 14

Test of Super Wetting Agent

A mixture of 10 g Sylgard base, 1 g Sylgard catalyst, and 0.55 g Q2-5211 was prepared, the base and catalyst being mixed first and the Q2-5211 being added subsequently. This mix was then spread over a PET liner at 0.60 mm thickness. The mix was cured for a period of hours at 165° F. The wet-out of the Q2-5211 sample was estimated by recording the spreading of a single drop of BSA (bovine serum albumin) casting solution through video. It was found that that there was a .about.260% increase in drop area compared to a control. The casting solution had the composition of Example 3, row A14.

EXAMPLE 15

Fabrication of Microneedle Arrays Using Super Wetting Agent

In order to test the value of a "super wetting agent," Dow Corning Q2-5211, with Sylgard 184 molds, the following tests were carried out. A mixture of 10 g Sylgard base, 1 g Sylgard catalyst, and 0.55 g Q2-5211 was prepared, the base and catalyst being mixed first and the Q2-5211 being added subsequently. This mix was then spread over a master microneedle array in order to prepare a mold. The mix on the master was placed under vacuum for 20 minutes and then cured for several hours at 155° F. Red food coloring was mixed with a BSA (bovine serum albumin) casting solution used in Example 3. Ten µL of this solution was pipetted onto the mold array. A half-inch-wide 30 mil thick piece of high impact polystyrene (HIPS) was used as a squeegee and the formulation was spread across the array several times.

The sample was placed on a small piece of Lexan® and vortexed for 5 seconds to homogenize the liquid layer and move entrapped air. The sample was placed in a pressure vessel and pressurized at 15 psi for 10 minutes. The sample was then removed and placed in a drying chamber for one hour. The sample was then removed and 75 μL of a second layer not containing BSA was spread over the back of the array using the squeegee. The sample was placed in the pressure vessel and pressurized at 15 psi for 2 minutes. The sample was removed and again placed in a drying chamber for one hour.

The array was removed from the mold by using a 17 mm button of 30 mil HIPS with double sided-adhesive on both sides of the button. One side of the button was adhered to a 17 mm diameter magnetic rod. The button was lowered on the array, gently compressed, then slowly removed while holding the silicone mold down. The button was then removed from the magnetic bar using a knife blade and the sample was adhered to a glass slide for better handling.

Microscopic examination of the array showed that the colored portion of the array was predominantly confined to the tips of the microprojections. This is attributed to superior wetting of the cast solutions on the mold on account of the inclusion of super wetting agent in the mold.

EXAMPLE 16

Solvent Casting of Polysulfone Microneedles

Microneedle arrays were made from polysulfone dissolved in dimethylformamide (DMF). Volumes of 150 and 200 μL were spread over a silicone mold to which a rim of PET was attached with PVP-PEG adhesive. The % solids in the casting solutions was 15 or 20%. The mold with casting solution was pressurized at 1 bar for 5 minutes. The whole was then placed in a 60° C. oven for periods ranging from 1 hour to overnight. The polysulfone was then demolded and the needles microscopically inspected. Air bubbles were seen in some cases, but other than the air bubbles, the microneedles appeared good.

EXAMPLE 17

Solvent Casting of Polystyrene Microneedles

Microneedle arrays were made from polystyrene dissolved in toluene. Volumes of 75 to 125 μL were spread over a silicone mold to which a rim of PET was attached with PVP-PEG adhesive. The % solids in the casting solutions was 15%. The mold with casting solution was pressurized at 1 bar for 5 minutes. The whole was then placed in a 60° C. oven for periods ranging from 2 to 3 h. The polystyrene was then demolded and the needles microscopically inspected. A small air bubble was seen in one case, but other than the air bubble, the microneedles appeared good.

EXAMPLE 18 hPTH (1-34) Stability in Dry Films Made with Microneedle Casting Formulations

Dry films of microneedle casting formulations were made using process conditions similar to those for casting microneedle arrays in order to evaluate the stability of hPTH (1-34 fragment) in the dried form. About 20 μL of liquid formulation is placed in an Eppendorf tube. The formulation is spread into a thin film in the inside wall of the tube, then dried at 32° C. for 30 min, and then further dried under vacuum at room temperature overnight. The dry films inside the Eppendorf tube were packaged in a polyfoil bag and stored at different temperatures for different durations. The purity of the hPTH(1-34) was analyzed by both reverse phase HPLC (rp-HPLC) and size exclusion HPLC (sec-HPLC). The details of the formulations are indicated in the table below.

The following table gives the details of formulations used to form dry films with hPTH as the drug.

| Ex. # | Polymer Type | Wt % | Sugar Type | Wt % | hPTH (1-34) Wt % | Solids in casting solution Wt % |
|---|---|---|---|---|---|---|
| F1 | PVA | 52.6 | Sucrose | 26.3 | 21.1 | 22.8 |
| F2 | Dextran 70 | 64.9 | Sorbitol | 19.5 | 15.6 | 30.8 |
| F3 | Tetrastarch | 64.9 | Sorbitol | 19.5 | 15.6 | 30.8 |
| F4* | Dextran 70 | 64.1 | Sorbitol | 19.4 | 15.4 | 31.2 |

*ca. 0.4 wt % of methionine is added to the formulation as an antioxidant agent.

Table A below illustrates the chemical purity as determined by rp-HPLC of the hPTH(1-34) in different formulations as a function of storage time at three different temperatures. Table B below illustrates the monomer content as determined by sec-HPLC of the hPTH(1-34) in different formulations as a function of storage time at three different temperatures. It appears that hPTH(1-34) is stable during storage for up to one month at even elevated temperature in all the formulations given in this example. (Formulation F3 was not sampled at the 1 week time point at room temperature or 40° C.)

TABLE A

| | F1 | F2 | F3 | F4 |
|---|---|---|---|---|
| 4° C. | | | | |
| t = 0 | 100.00 | 100.00 | 100.00 | 100.00 |
| t = 1 wk | 99.77 | 99.87 | 99.78 | 100.00 |
| t = 2 wk | 99.76 | 99.71 | 99.65 | 99.74 |
| t = 1 mo | 99.78 | 99.69 | 99.66 | 99.73 |
| Room Temp. | | | | |
| t = 0 | 100.00 | 100.00 | 100.00 | 100.00 |
| t = 1 wk | 99.75 | 100.00 | | 100.00 |
| t = 2 wk | 99.72 | 99.63 | 99.49 | 99.70 |
| t = 1 mo | 99.72 | 99.59 | 99.52 | 99.67 |
| 40° C. | | | | |
| t = 0 | 100.00 | 100.00 | 100.00 | 100.00 |
| t = 1 wk | 99.72 | 99.79 | | 99.88 |
| t = 1 mo | 99.56 | 99.14 | 98.64 | 99.39 |

TABLE B

| | F1 | F2 | F3 | F4 |
|---|---|---|---|---|
| 4° C. | | | | |
| t = 0 | 100.00 | 100.00 | 100.00 | 100.00 |
| t = 1 wk | 99.77 | 99.87 | 99.78 | 100.00 |
| t = 2 wk | 99.76 | 99.71 | 99.65 | 99.74 |
| t = 1 mo | 99.78 | 99.69 | 99.66 | 99.73 |

TABLE B-continued

|  | F1 | F2 | F3 | F4 |
|---|---|---|---|---|
| Room Temp. | | | | |
| t = 0 | 100.00 | 100.00 | 100.00 | 100.00 |
| t = 1 wk | 99.75 | 100.00 | | 100.00 |
| t = 2 wk | 99.72 | 99.63 | 99.49 | 99.70 |
| t = 1 mo | 99.72 | 99.59 | 99.52 | 99.67 |
| 40° C. | | | | |
| t = 0 | 100.00 | 100.00 | 100.00 | 100.00 |
| t = 1 wk | 99.72 | 99.79 | | 99.88 |
| t = 1 mo | 99.56 | 99.14 | 98.64 | 99.39 |

It is claimed:

1. A microprotrusion array, comprising:
an approximately planar base and a plurality of microprotrusions, wherein the microprotrusions comprise at least a first and a second layer arranged roughly parallel to the plane of the planar base, the first and second layers formed of different polymers, the first layer is contained in a distal end of the microprotrusions and comprised of (i) a biodegradable polymer, (ii) one or more components to facilitate biodegradation selected from sugars, sugar alcohols, cyclodextrins and water-swellable polymers, and (iii) an active ingredient, wherein a ratio of weight percent of the biodegradable polymer to weight percent of the one or more components to facilitate biodegradation is in the range of about 6.25:1 to about 1:3.75.

2. The array of claim 1, wherein the second layer is comprised of a polymer that is biodegradable.

3. The array of claim 1, wherein at least the first layer comprises at least one of polyvinyl alcohol, dextran, and hydroxyethyl starch.

4. The array of claim 1, wherein the sugar is selected from dextrose, fructose, galactose, maltose, maltylose, isomaltulose, mannose, lactose, lactulose, sucrose and trehalose.

5. The array of claim 1, wherein the sugar alcohol is selected from sorbitol, lactitol, malitol or mannitol.

6. The array of claim 1, wherein at least the first layer comprises at least one antioxidant.

7. The array of claim 6, wherein the antioxidant is selected from methionine, cysteine, D-alpha tocopherol acetate, DL-alpha tocopherol, ascorbyl palmitate, ascorbic acid, butylated hydroxyanisole, butylated hydroxyquinone, hydroxycomarin, butylated hydroxytoluene, cephalin, ethyl gallate, propyl gallate, octyl gallate, lauryl gallate, propylhydroxybenzoate, trihydroxybutyrophenone, dimethylphenol, ditert-butylphenol, vitamin E, lecithin or ethanolamine.

8. The array of claim 1, wherein at least one of the first and second layers comprises an antimicrobial.

9. The array of claim 8, wherein the antimicrobial is chosen from the group consisting of benzalkonium chloride, benzyl alcohol, chlorbutanol, meta cresol, esters of hydroxyl benzoic acid, phenol, and thimerosal.

10. The array of claim 1, wherein a layer of the first and second layers comprises cellulose acetate butyrate, cellulose acetate, cellulose acetate propionate, ethyl cellulose, nitrocellulose, hydroxypropyl methyl cellulose phthalate, a polyacrylate, a polymethacrylate, a poly(hydroxyl alkanoate), poly(lactic acid), poly(glycolic acid), poly(lactic acid-co-glycolic acid), a polycaprolactone, or copolymers thereof.

11. The array of claim 1, wherein the active ingredient comprises a polypeptide, a protein, or a nucleic acid.

12. The array of claim 11, wherein the active ingredient is selected from a vaccine, a therapeutic antibody or parathyroid hormone.

13. The array of claim 1, wherein the array achieves a skin penetration efficiency of at least about 80%.

14. The array of claim 1, wherein at least one microprotrusion has a cross sectional diameter in a plane parallel to that of the base which decreases as a function of the distance of the plane parallel from the base in such a way that the cross sectional diameter decreases more rapidly near the base than further away from it.

15. The array of claim 1, wherein at least some of the microprotrusions detach from the base following insertion into skin.

16. The array of claim 1, wherein the rate at which portions of the microprotrusions degrade is dependent on the pH of the environment in which the portions of the microprotrusions find themselves following insertion.

17. The array of claim 1, wherein the first layer comprises a composition which degrades at different rates at different temperatures in the range of about 25° C. to about 40° C.

18. The array of claim 1, wherein the biodegradable polymer in the first layer is dextran, the component to facilitate biodegradation is sorbitol, and the active ingredient is parathyroid hormone.

* * * * *